United States Patent
Ahn et al.

(10) Patent No.: US 8,980,846 B2
(45) Date of Patent: Mar. 17, 2015

(54) COMPOSITION CONTAINING STYRAXLIGNOLIDE A OR THE AGLYCONE THEREOF AS AN ACTIVE INGREDIENT FOR PREVENTING OR TREATING ASTHMA

(75) Inventors: Kyung Seop Ahn, Daejeon (KR); Ha Young Jang, Daejeon (KR); Sei Ryang Oh, Daejeon (KR); Hyeong Kyu Lee, Daejeon (KR); Ok-Kyoung Kwon, Daejeon (KR); Semi Kim, Daejeon (KR); Jung Hee Kim, Daejeon (KR); Doo-Young Kim, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 13/885,986

(22) PCT Filed: Nov. 17, 2011

(86) PCT No.: PCT/KR2011/008805
§ 371 (c)(1),
(2), (4) Date: May 16, 2013

(87) PCT Pub. No.: WO2012/067447
PCT Pub. Date: May 24, 2012

(65) Prior Publication Data
US 2013/0244959 A1 Sep. 19, 2013

(30) Foreign Application Priority Data

Nov. 17, 2010 (KR) ........................ 10-2010-0114672
Nov. 17, 2011 (KR) ........................ 10-2011-0120160

(51) Int. Cl.
| | | |
|---|---|---|
| A61K 31/70 | (2006.01) |
| A61K 31/34 | (2006.01) |
| A61K 31/7048 | (2006.01) |
| A61K 31/343 | (2006.01) |
| A61K 36/185 | (2006.01) |
| A23L 1/30 | (2006.01) |

(52) U.S. Cl.
CPC ............ *A61K 31/7048* (2013.01); *A61K 31/343* (2013.01); *A61K 36/185* (2013.01); *A23L 1/3002* (2013.01); *A23V 2002/00* (2013.01)
USPC ............................................. 514/25; 514/469

(58) Field of Classification Search
CPC ........................ A61K 31/7048; A61K 31/343
USPC .................................................... 514/25, 469
See application file for complete search history.

(56) References Cited

PUBLICATIONS

Asher et al. (1998) "International Study of Asthma and Allergy in Childhood," *Clin. Exp. Allergy.* 28(Suppl. 5):52-56.

Barnes et al. 1998 "Inflammatory Mediators of Asthma: An Update," *Pharmacol. Rev.* 50:515-596.
Elias et al. (2003) "New Insights into the Pathogenesis of Asthma," *J. Clin. Invest.* 111:291-297.
Garcia Garcia et al. (2005) "Montelukast, Compared with Fluticasone, for Control of Asthma Among 6- to 14-Year-Old Patients with Mild Asthma: The Mosaic Study," *Pediatrics.* 116(2):360-369.
International Search Report and Written Opinion corresponding to International Application No. PCT/KR2011/008805, mailed May 21, 2012.
Jeffery et al. (1992) "Effects of Treatment on Airway Inflammation and Thickening of Reticular Collagen in Asthma: a Quantitative Light and Electron Microscopic Study," *Am. Rev. Respir. Dis.* 145:890-899.
Maggi (1998) "The TH1/TH2 Paradigm in Allergy," *Immunotechnology.* 3:233-244.
Pawankar (2001) "Mast Cells as Orchestrators of the Allergic Reaction: The IgE-IgE Receptor Mast Cell Network," *Curr. Opin. Allergy Clin. Immunol.* 1:3-6.
Warshmana et al. (1998) "Dexamethasone Activates Expression of the PDGF-α Receptor and Induces Lung Fibroblast Proliferation," *Am. J. Physiol.* 274:499-507.
Wuthrich (1989) "Epidemiology of the Allergic Diseases: Are They Really on the Increase?" *Int. Arch. Allergy Appl. Immunol.* 90:3-10.
Yang et al. (2007) "Synthesis of 2-Aryl-5-Alkyl-7-Methoxylbenzo[b]furan Derivatives," *Chinese Chemical Letters.* 18:380-382.
B.-S. Min et al., "Anti-complement activity of Norlignans and Terpenes from the stem bark of Styrax japonica," Planta Med 70:1210-1215, 2004.
M. Wills-Karp, "Complement activation pathways. A bridge between innate and adaptive immune responses in asthma," Proc Am Thorac Soc 4:247-251, 2007.
P. M. Pauletti et al., "The Styracaceae," Brazilian Journal of Pharmacognosy 16(4):576-590, Dec. 2006.

*Primary Examiner* — Elli Peselev
(74) *Attorney, Agent, or Firm* — Lathrop & Gage LLP

(57) ABSTRACT

The present invention relates to a pharmaceutical composition for preventing or treating asthma, the composition containing styraxlignolide A or an aglycone thereof as an active ingredient. More particularly, styraxlignolide A compound is one separated from stems and barks of *Styrax japonica*, and styraxlignolide A or homoegonol, which is an aglycone of styraxlignolide A and which has improved safety, has the effect of attenuating weight loss and airway hyperresponsiveness, inhibiting the generation of reactive oxygen species in airway, inhibiting generation of IgE, TGF-β1, and IL-17 in the serum and bronchoalveolar lavage fluid, inhibiting endobronchial inflammatory cell infiltration, and inhibiting the formation of a mucous plug and subepithelial fibrosis in an asthma-induced mouse model. Therefore, styraxlignolide or homoegonol can be effectively used as the active ingredient of a pharmaceutical composition for preventing or treating bronchial asthma in which airway remodeling has progressed.

5 Claims, 20 Drawing Sheets

Fig. 4
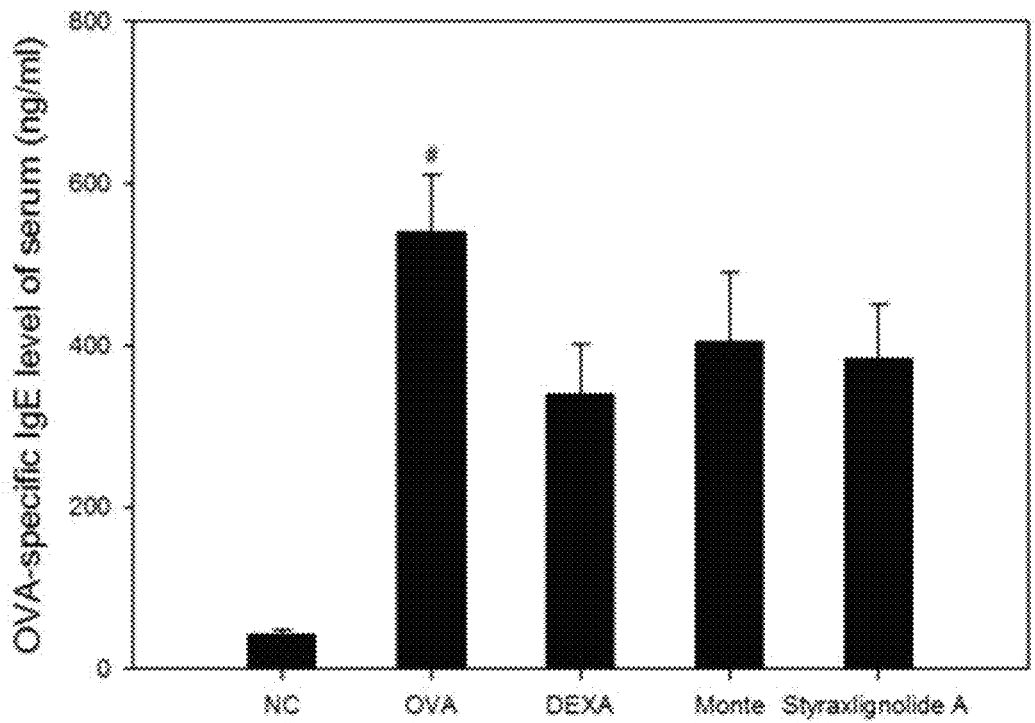
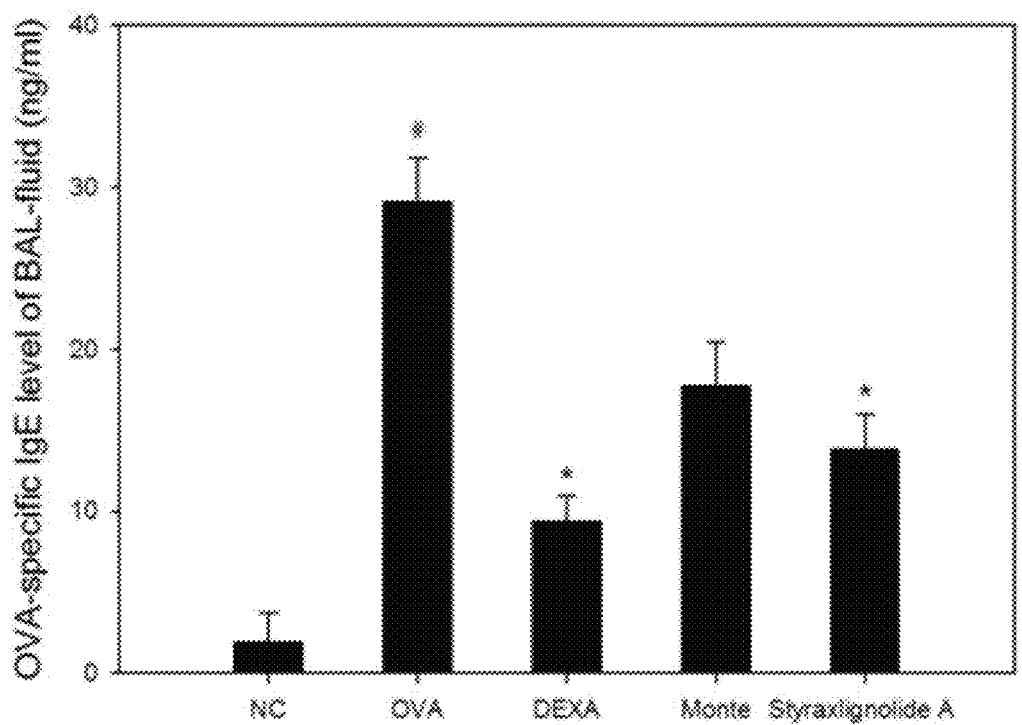

Fig. 20
Step1
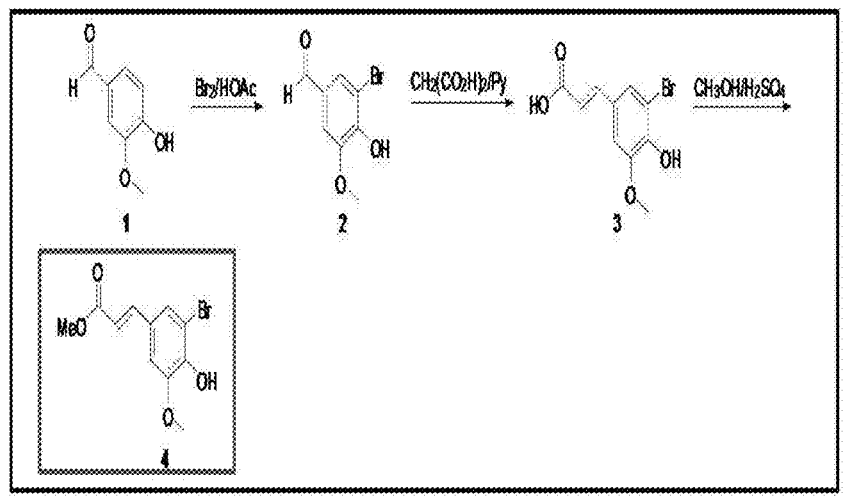
Step2
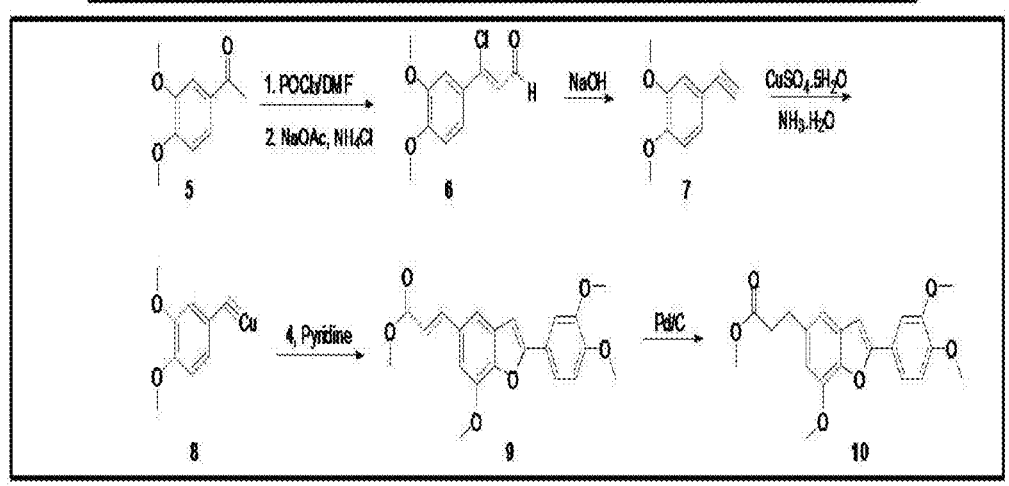
Step3
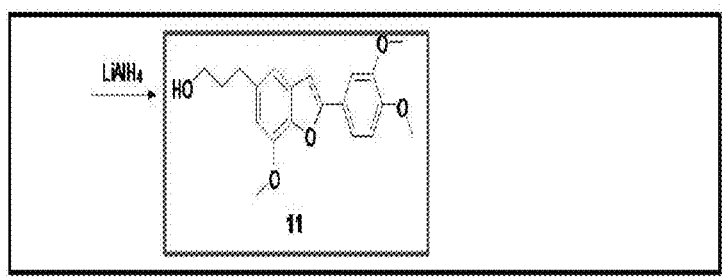

COMPOSITION CONTAINING STYRAXLIGNOLIDE A OR THE AGLYCONE THEREOF AS AN ACTIVE INGREDIENT FOR PREVENTING OR TREATING ASTHMA

CROSS-REFERENCE TO RELATED APPLICATIONS

This application is a U.S. National Stage Application under 35 U.S.C. §371 of International Application No. PCT/KR2011/008805, filed Nov. 17, 2011, which claims the benefit of Korean Application No. 10-2011-0114672, filed Nov. 17, 2010; and Korean Application No. 10-2011-0120160, filed Nov. 17, 2011. All of these applications are hereby incorporated by reference in their entireties.

BACKGROUND OF THE INVENTION

1. Field of the Invention

The present disclosure relates to a composition for preventing or treating asthma, the composition containing styraxlignolide A or an aglycone thereof as an active ingredient.

2. Description of the Related Art

Allergic diseases of which incidence rate is globally on the increase include anaphylaxis, allergic rhinitis, asthma, atopic dermatitis and urticaria (Wuthrich B. Int. Arch. Allergy Appl. Immunol., 90, pp 3-10, 1989).

Among these allergic diseases, asthma is a chronic inflammatory respiratory disease, from which about 3 million people in Republic of Korea are estimated to suffer, and which is characterized by symptoms of cough, wheezing, that is a high-pitched whistling sound during breathing, shortness of breath, chest tightness, and the number of patients has lately increased suddenly due to intensified atmospheric pollution, and westernization of dietary life. Asthma is the most common disease in the more developed countries such as the United States, the United Kingdom, and it is estimated that 20-30% of the total population are patients. In Republic of Korea, 16% of primary school children, about 5% of adults, and total 4 million or more are estimated to be patients, and asthma is a common disease, which can be seen in all age groups from early childhood or childhood to the elderly and 10% of total population suffer from. For the cause, atopic constitution which causes allergy in a family was identified to be a basic factor, and airway hyperresponsiveness, eosinophil inflammation in airway, and accentuation of Th2 immune response are reported to be basic factors. Due to asthma, difficulty in breathing, severe coughs, and wheezing (a high-pitched whistling sound during breathing) occur, and according to WHO's special report published in 2000, 150 million patients suffer from asthma worldwide, and 180,000 die of bronchial asthma each year. Furthermore, WHO's special report commented that the disease prevalence rate and severity are continuously on an increasing trend, and medical and social costs due to asthma surpass those for pulmonary tuberculosis and AIDS combined.

In case of Republic of Korea, the prevalence rate of childhood asthma was only 3-4% in early 1980s, and increased 2-fold or more. According to 'ISAAC (International Study of Asthma and Allergy in Childhood)' published in 1998, the prevalence rate of childhood asthma was 13.3% in Korean children aged 6-7-years, and 7.7% in children aged 13-14 years. Taken those children as a whole, ten out of one hundred children suffer from asthma, and five, 50% of them, would suffer from asthma for terms of life. Not only the prevalent rate but also severity of the disease worsens the seriousness of the problem.

Asthma is generally recognized as chronic inflammatory disease which is caused by the migration and infiltration of inflammatory cells proliferated, differentiated, and activated by interleukin-4, 5, and 13 generated by TH2 immunocytes into and around the airway (Elias J A, et al., *J. Clin. Invest.*, 111, pp 291-297, 2003). At this time, the activated inflammatory cells such as eosinophils, mast cells and alveolar macrophages secret various inflammation mediators (cysteinyl leukotriene, prostaglandin, etc), which play a critical role in bronchoconstriction (Maggi E., *Immunotechnology*, 3, pp 233-244, 1998; Pawankar R., *Curr. Opin. Allergy Clin. Immunol.*, 1, pp 3-6, 2001; Barnes P J, et al., *Pharmacol Rev.*, 50, pp 515-596, 1998).

Productions of cytokines involved in the activation of inflammatory cells such as IL-4, IL-5, and IL-13, and immunoglobulin E, as well as biosynthesis of cysteinyl leukotriene secreted from inflammatory cells such as eosinophils mediated by the cytokines and immunoglobulin E are major causes of inflammation and allergic reaction and asthma caused by such inflammation and allergic reaction. Therefore, studies are actively undergoing to develop drugs to inhibit their productions.

Currently, various therapeutic agents are commercially available, but a lot of therapeutic agents have side effects and require caution when using. Inhalation corticosteroid preparations are still the most important therapeutic agent, and exhibit excellent effects, but they are known to result in adrenal suppression, bone density decrease, failure to thrive, ocular and skin complications, etc. when using for long time in proportion to doses and use time. In addition, there is a report that corticosteroids can rather increase collagen synthesis (Warshmana G S, et al., Am J Physiol 274, 499-507, 1998). Thus, in spite of corticosteroid treatment for several years for patients with chronic persistent asthma, there are few patients with asthma whose hyperresponsiveness is normalized. Long-term administration of beta-2 agonists are known not to inhibit airway remodeling (Jeffery P K, et al., *Am Rev Respir Dis* 145: 890-0, 1992), and it has been warned that long-acting beta-2 agonists such as salmeterol and formeterol prevent asthmatic attack, and rather can result in deaths in patients with asthma. These various adverse effects have been reported, but have been continuously prescribed under the conclusion that their effects of alleviating asthmatic symptoms are larger than risks of adverse effects. When the growth quotient of children asthmatic patients who are sensitive to adverse effects was measured, the growth quotient of children asthmatic patients who took oral leukotriene antagonist (montelukast) was shown to be superior to that of children asthmatic patients who used inhalation corticosteroid up to 1 cm per year (Garcia Garcia M L, et al., *Pediatrics* 116(2): 360-9, 2005). If asthma is not controlled in the growing period, the growth of overall body as well as lung can be inhibited, and thus, maintaining normal lung function through continued treatment is essential for growth, but it was identified that nothing is more important than to use a safe drug for continued treatment and care for respiratory inflammation. Thus, when choosing therapeutic agents, adverse effects as well as effects of alleviating asthma should be considered carefully. Leukotriene antagonists are known to have a low frequency of adverse effects, and are newly used for preventing asthma and continued treatment. However, their effects of alleviating asthma are weaker than other drugs, and they show remarkable effects only in one-third of patients. Therefore, development of novel therapeutic agents for asthma which are nontoxic and safe, and can prevent drug resistance is required.

*Styrax japonica* is a tree in the Styracaceae family, Ericales, and is native to Korea, China, and Japan, and is a deciduous tall tree. It grows up to approximately 10 to 15 m tall, and is very resistant to cold and pollution. The bark is dark brown, and leaves are alternate, egg-shaped or long-oval shape, and pointed at the end. Fruits are drupaceous, ripen in September, oval shape, and when ripe, the skin splits irregularly. For components of *Styrax japonica*, about 10% of egosaponin is in the fruit skin, various kinds of glycerides, fatty oil, and egonol are in seeds, and saponin is in flowers. *Styrax japonica* is called as Maemadeung, Jedongwa, and is used medicinally. In oriental medicine, *Styrax japonica* is used for getting rid of intestinal worms, killing insects, discharge of irritable phlegm, laryngitis, preservatives, etc., and is known to have efficacies in cyanidation, airing and dehumidification, and treat afterpain, Atong (toothache), Chitong (toothache), arthritis due to wind-dampness, melagia, etc.

Thus, the present inventors have been focused on herb medicine in the light of adverse effects and safety in a living body, and above all, the present inventors have performed research to develop therapeutic agents for asthma, which are capable of being used for long-term treatment and have an inhibitory effect on airway remodeling, identified that styraxlignolide A isolated from *Styrax japonica* or its aglycone homoegonol have excellent inhibiting effects on airway hyperresponsiveness, endobronchial infiltration of inflammatory cells, and progress of airway remodeling (bronchial epithelial cell thickening, mucous secretory cell hyperplasia, progress of fibrosis) in an asthma-induced model, compared to the current widely used drugs for asthma, dexamethasone or montelukast, and proved that styraxlignolide A or homoegonol can be used as an active ingredient of a compound for preventing or treating asthma, thereby leading to completion of the present invention.

SUMMARY OF THE INVENTION

One object of the present invention is to provide a pharmaceutical composition for preventing or treating asthma, the composition containing styraxlignolide A, an aglycone or a pharmaceutically acceptable salt thereof as an active ingredient.

In order to achieve the object, the present invention provides a pharmaceutical composition for preventing and treating asthma, the composition containing styraxlignolide A compound represented by the following Chemical Formula 1, the aglycone thereof represented by the following Chemical Formula 2, or a pharmaceutically acceptable salt thereof as an active ingredient:

The present invention also provides a health food composition for preventing and alleviating asthma, the health food composition containing styraxlignolide A compound represented by the above Chemical Formula 1, the aglycone thereof represented by the above Chemical Formula 2, or a pharmaceutically acceptable salt thereof as an active ingredient.

The present invention discloses novel effects of Styraxlignolide A compound or its aglycone homoegonol on asthma, which have never been disclosed in a conventional art. Because it was found that styraxlignolide A or homoegonol according to the present invention have excellent inhibiting effects on airway hyperresponsiveness, endobronchial infiltration of inflammatory cells, and progress of airway remodeling (bronchial epithelial cell thickening, mucous secretory cell hyperplasia, progress of fibrosis) in an asthma-induced model, compared to the current widely used drugs for asthma, dexamethasone or montelukast, and styraxlignolide A or homoegonol according to the present invention have low toxicity, styraxlignolide A or homoegonol according to the present invention can be used effectively for prevention or treatment of bronchial asthma, such as in cases of showing resistance to steroids, showing progress of airway remodeling, or requiring long-term use of therapeutic agents for asthma.

BRIEF DESCRIPTION OF THE DRAWINGS

The above and other objects, features and other advantages of the present invention will be more clearly understood from the following detailed description taken in conjunction with the accompanying drawings, in which.

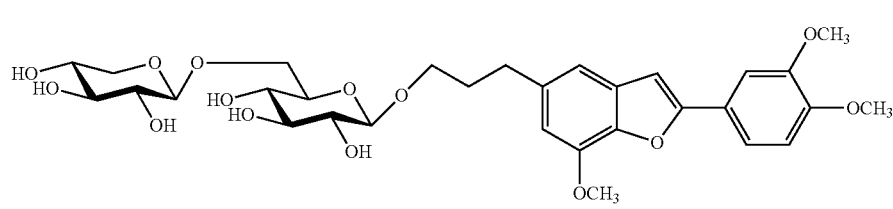

[Chemical Formula 1]

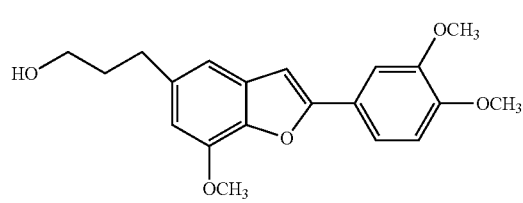

[Chemical Formula 2]

FIG. 4 is a graph illustrating ovalbumin-specific IgE concentration in serum or bronchoalveolar lavage fluid for each experimental group.

Figure 5:
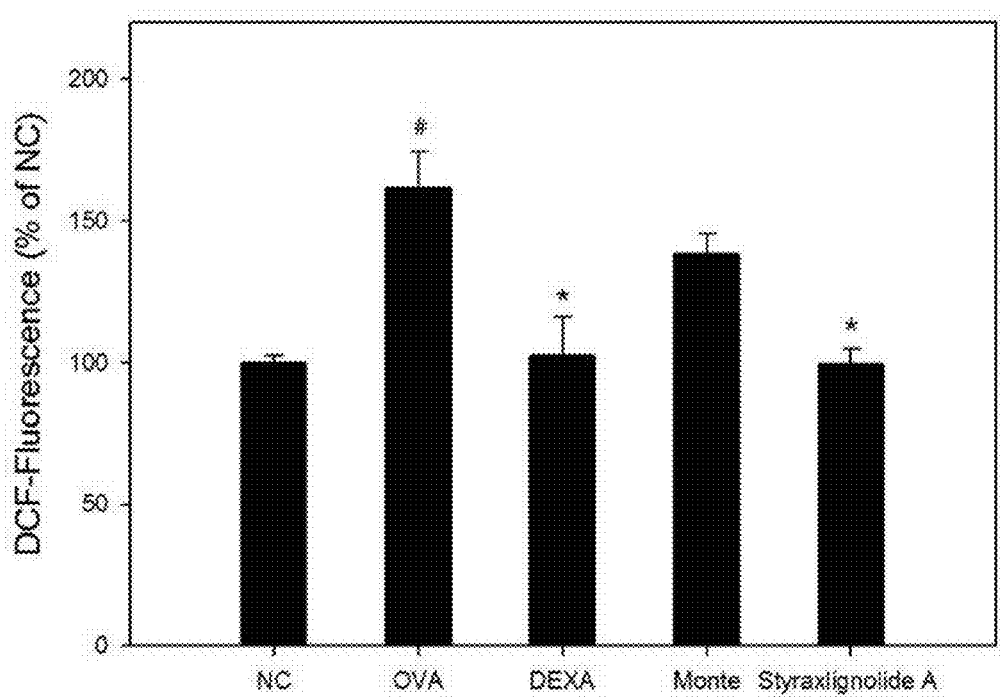

FIG. 5 is a graph illustrating the generated amount of reactive oxygen species in bronchoalveolar lavage fluid for each experimental group.

Figure 6:
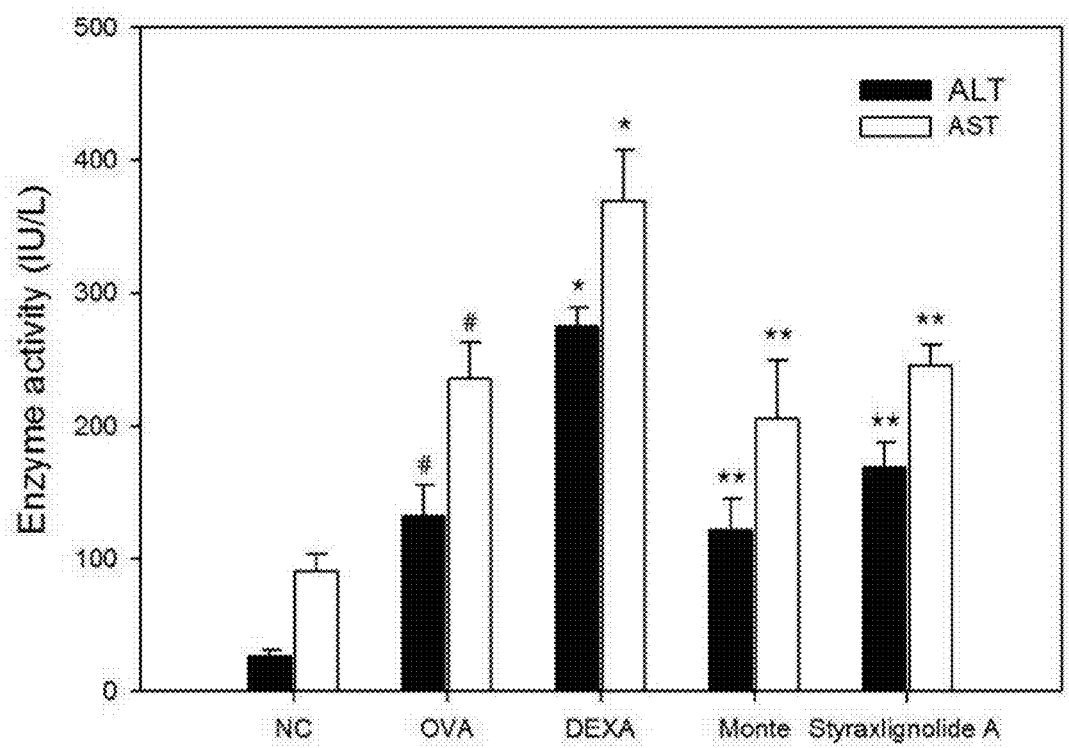

FIG. 6 is a graph illustrating the measured liver toxicity for each experimental group (hereinafter, **: statistically significant compared to the dexamethasone-administration group (DEXA)($p<0.05$)).

Figure 7:
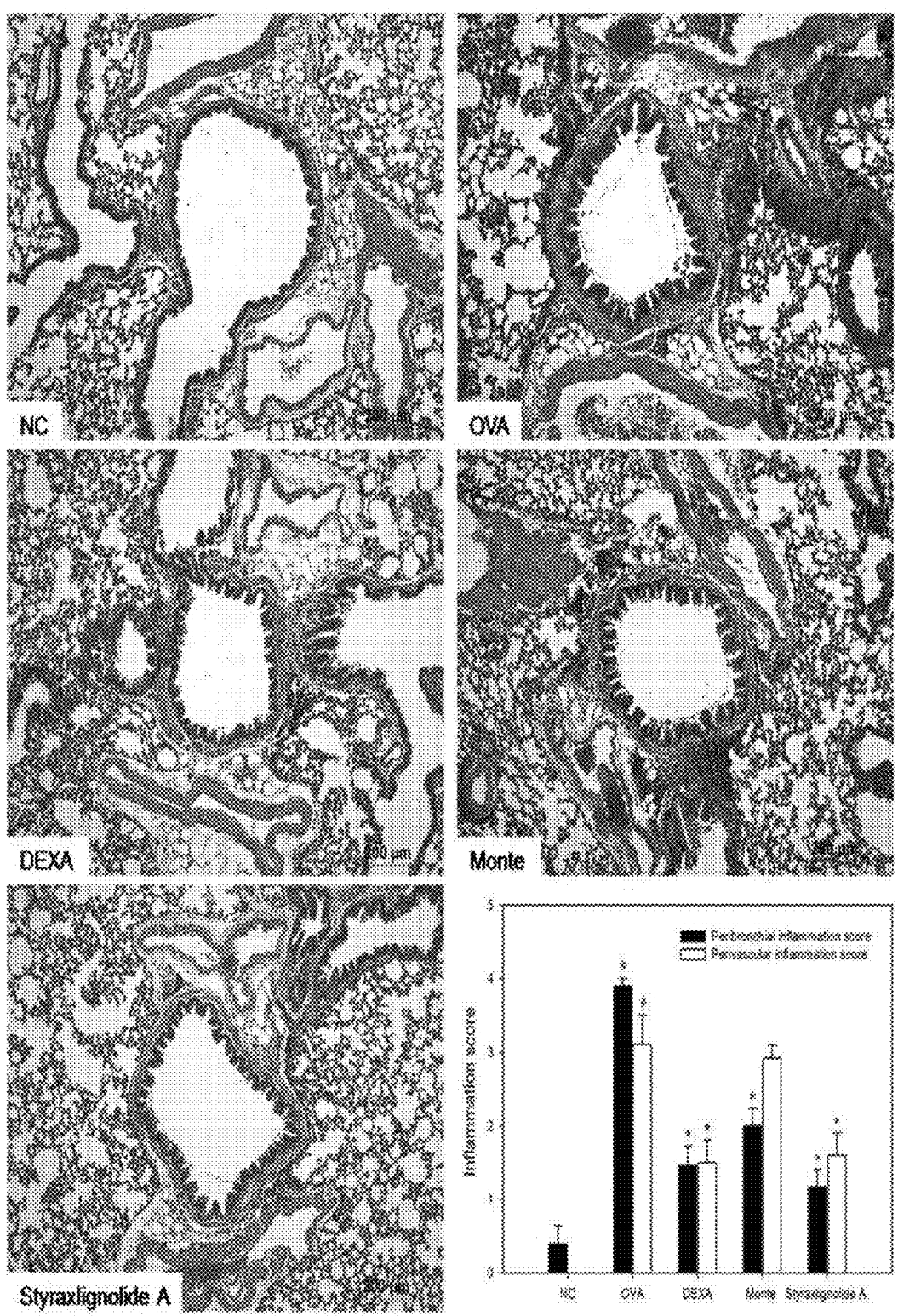

FIG. 7 is a drawing showing inflammatory cell infiltration in airway mucosa and inflammatory index for each experimental group.

Figure 8:
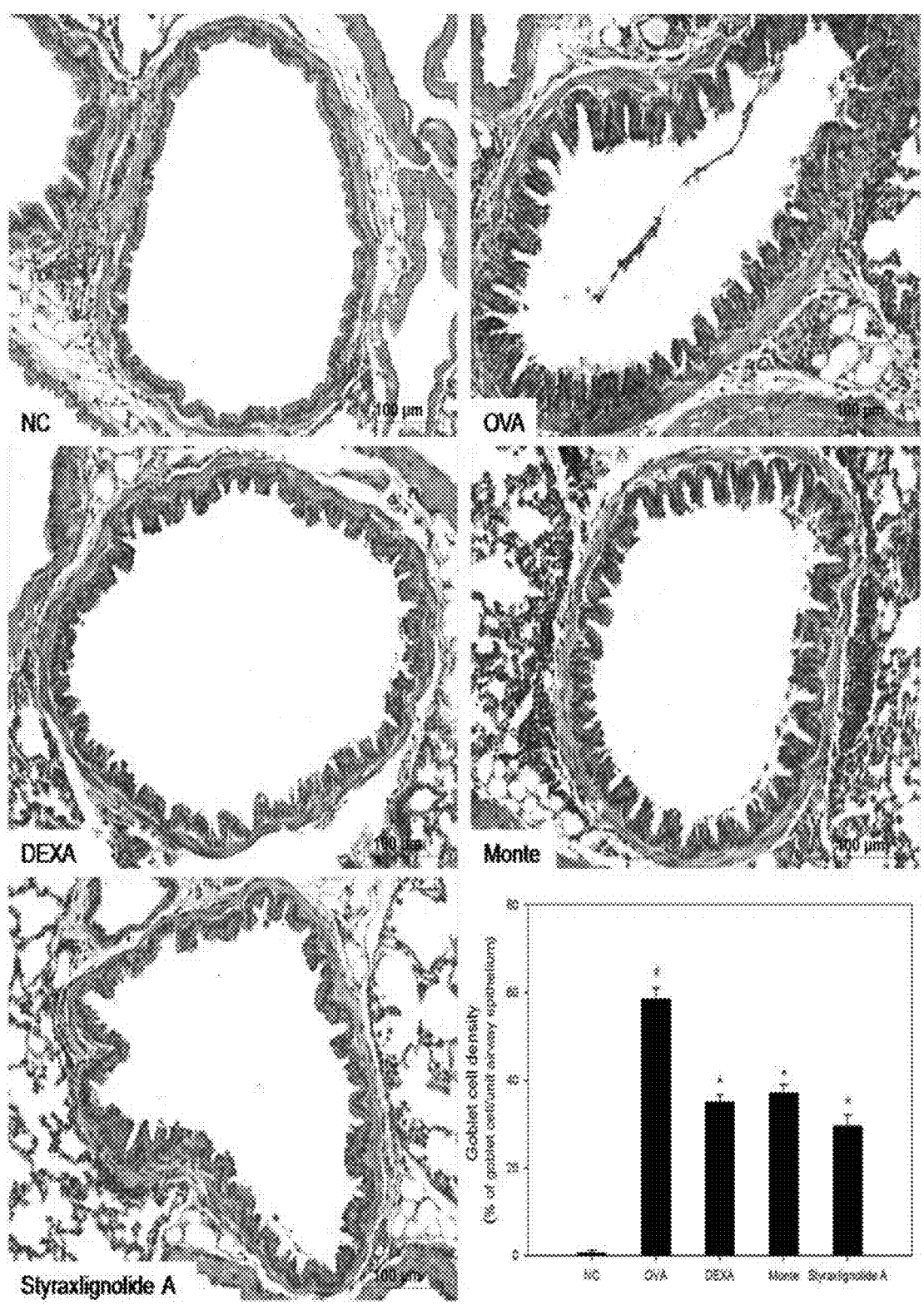

FIG. 8 is a drawing showing the ratio of goblet cells for each experimental group.

Figure 9:
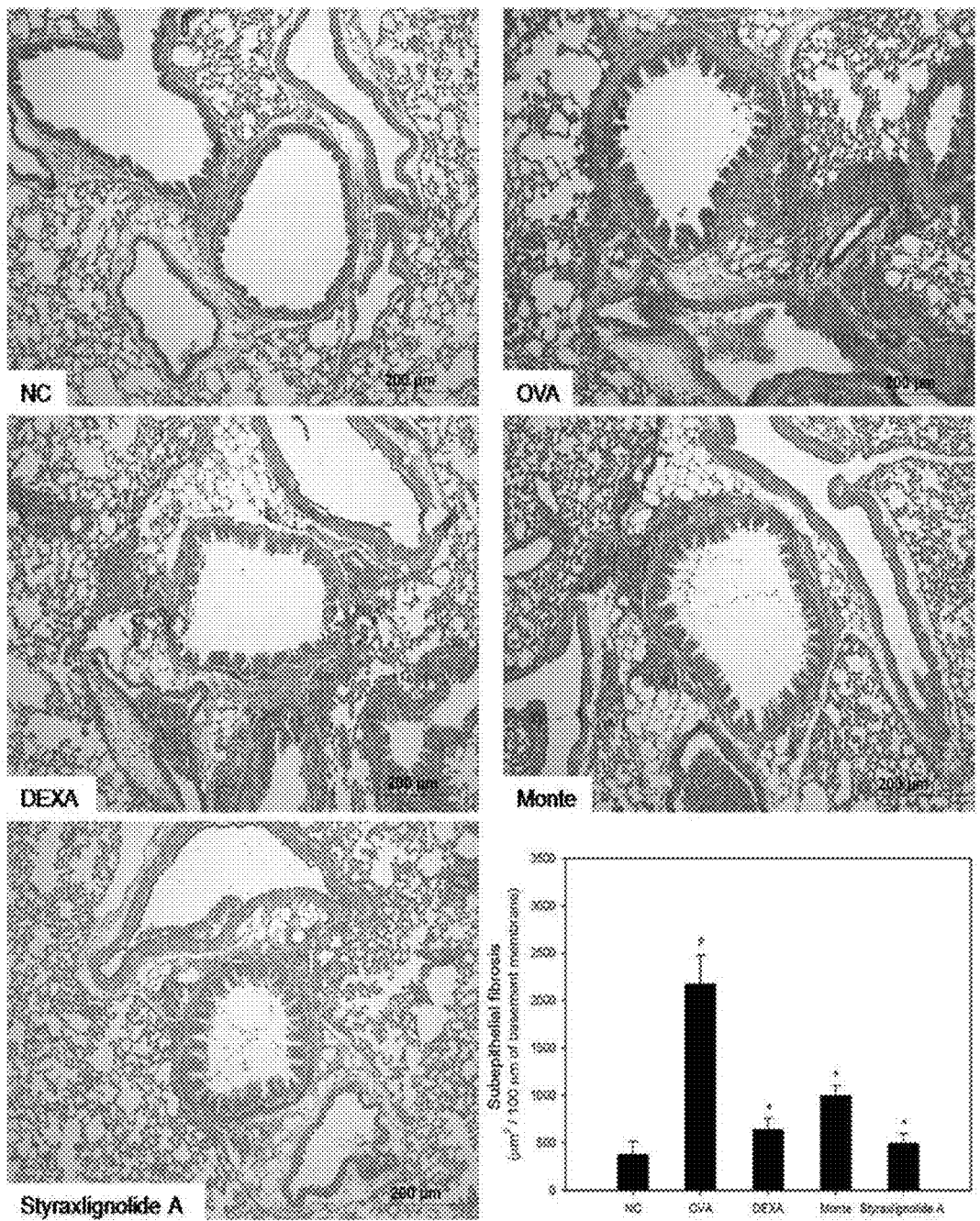

FIG. 9 is a drawing showing regions of subepithelial fibrosis for each experimental group.

Figure 10:
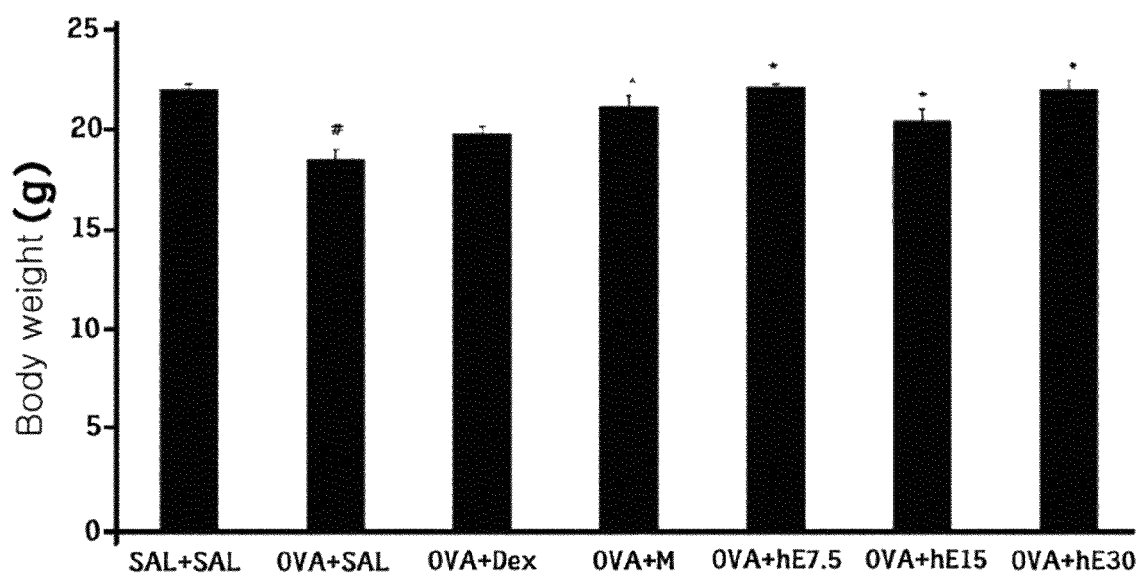

FIG. 10 is a graph illustrating the measured body weights for a normal control group (SAL+SAL), an asthma-induced group (OVA+SAL), a Dexamethasone-administered asthma-induced group (OVA+Dex), a montelukast-administered asthma-induced group (OVA+M), and a 7.5 mg of homoegonol-administered asthma-induced group (OVA+hE7.5), a 15 mg of homoegonol-administered asthma-induced group (OVA+hE15), and a 30 mg of homoegonol-administered asthma-induced group (OVA+hE30).

Figure 11:
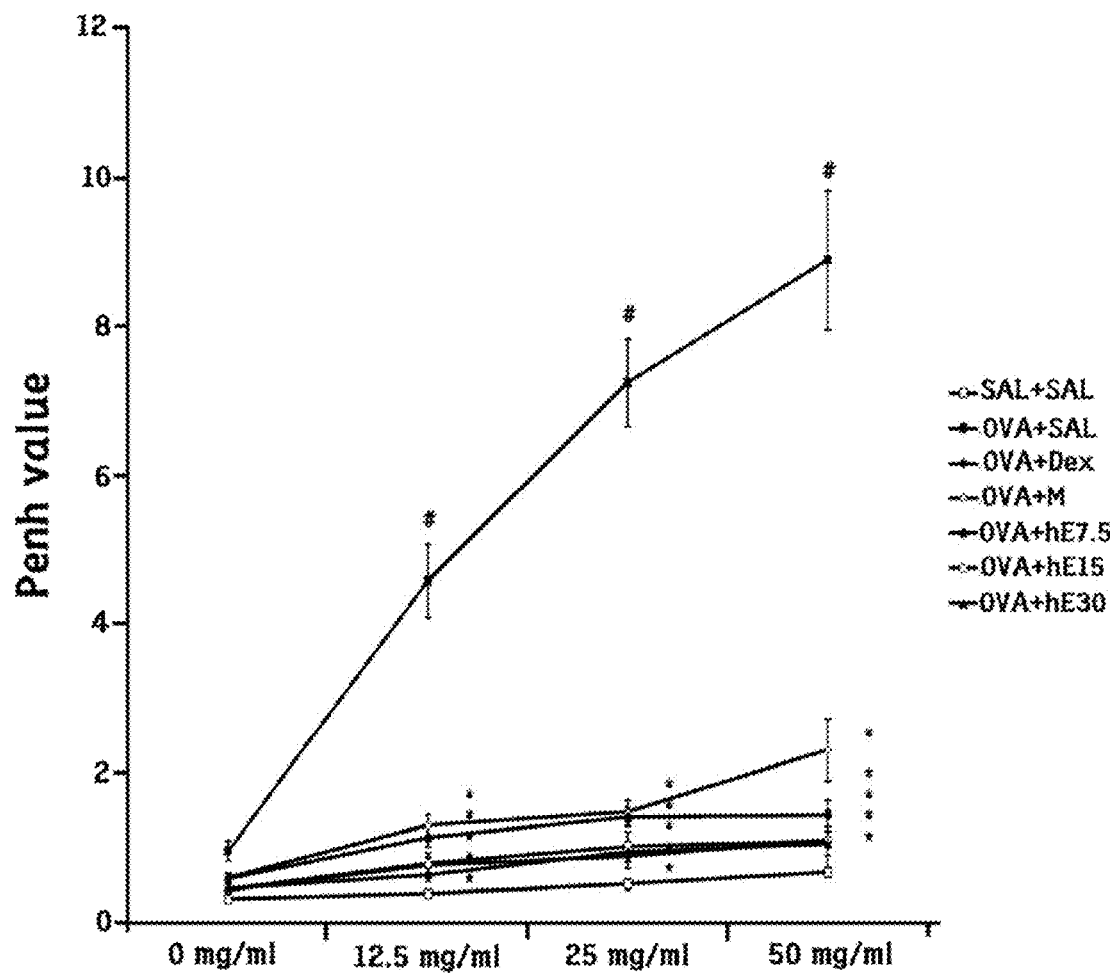

FIG. 11 is a graph illustrating airway hyperresponsiveness for each experimental group as Penh (enhanced pause) value, the degree of airway resistance.

Figure 12:
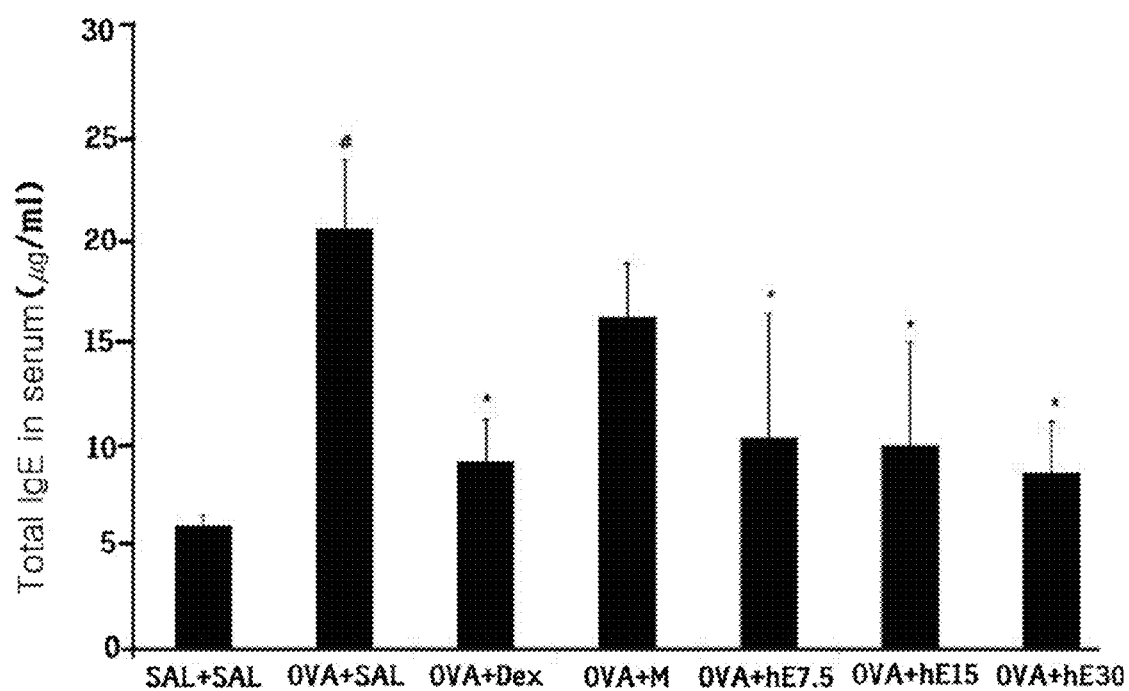

FIG. 12 is a graph illustrating serum ovalbumin-specific IgE concentration for each experimental group.

Figure 13:
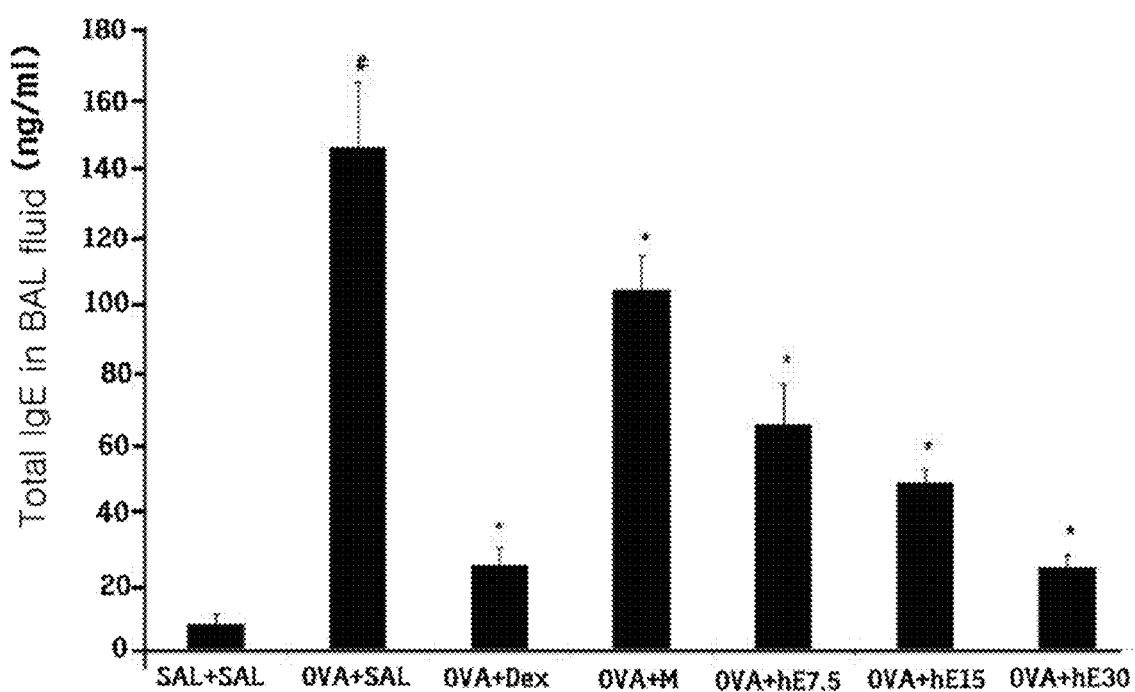

FIG. 13 is a graph illustrating ovalbumin-specific IgE concentration in bronchoalveolar lavage fluid for each experimental group.

Figure 14:
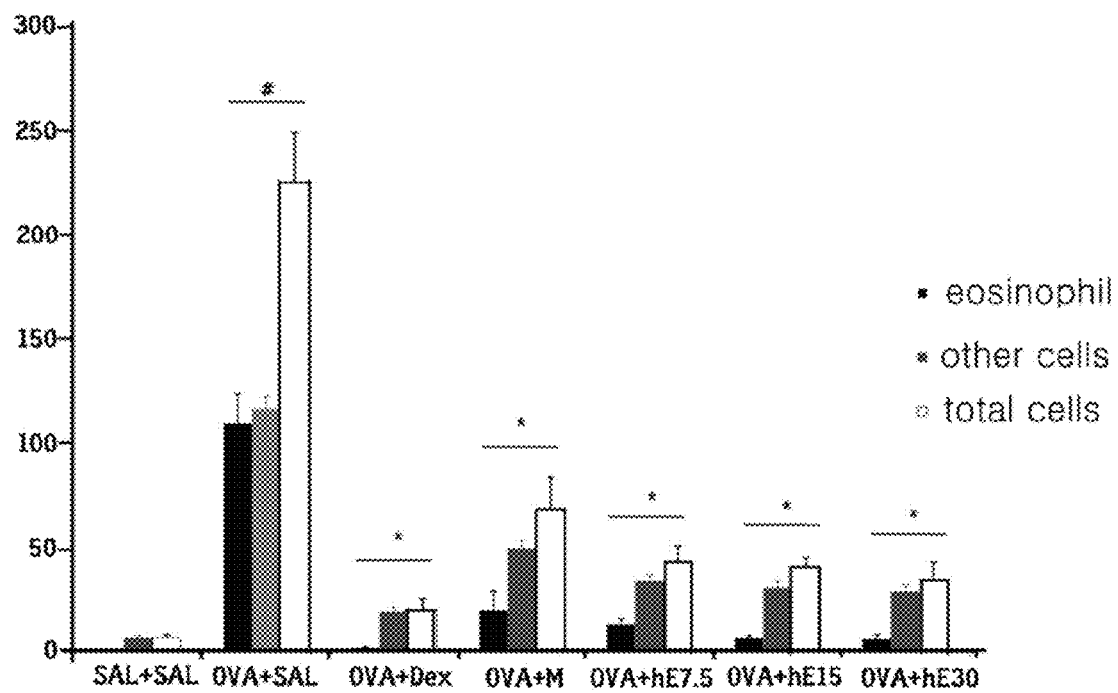

FIG. 14 is a graph illustrating the number of inflammatory cells in bronchoalveolar lavage fluid for each experimental group.

Figure 15:
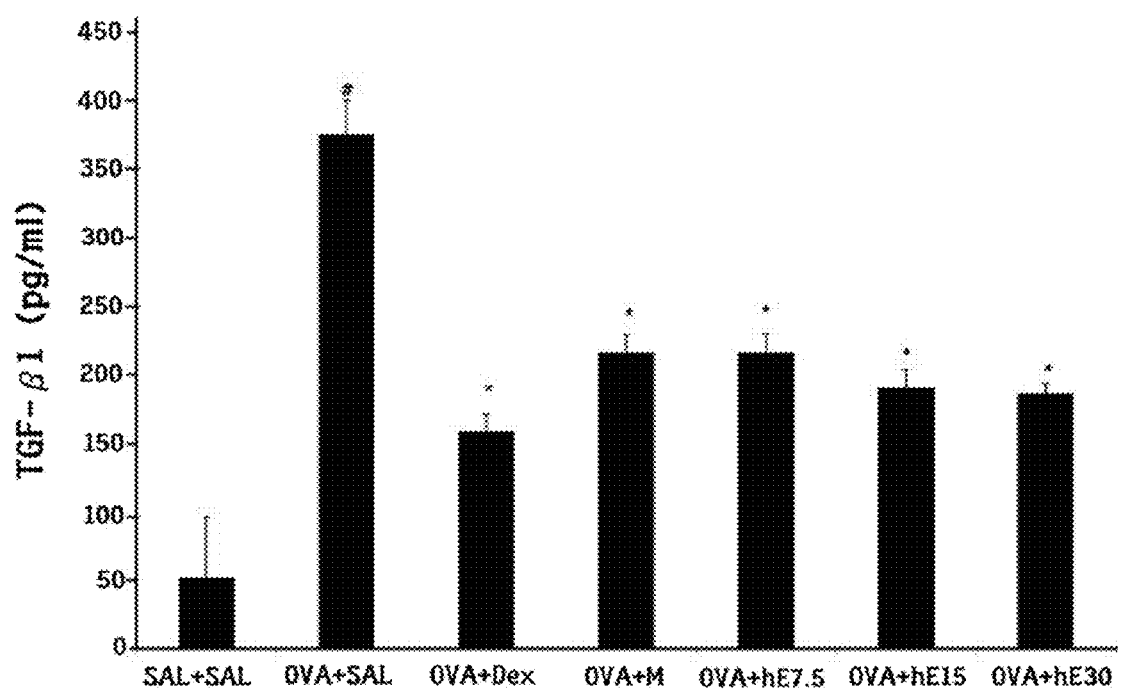

FIG. 15 is a graph illustrating TGF-β1 concentration in bronchoalveolar lavage fluid for each experimental group.

Figure 16:
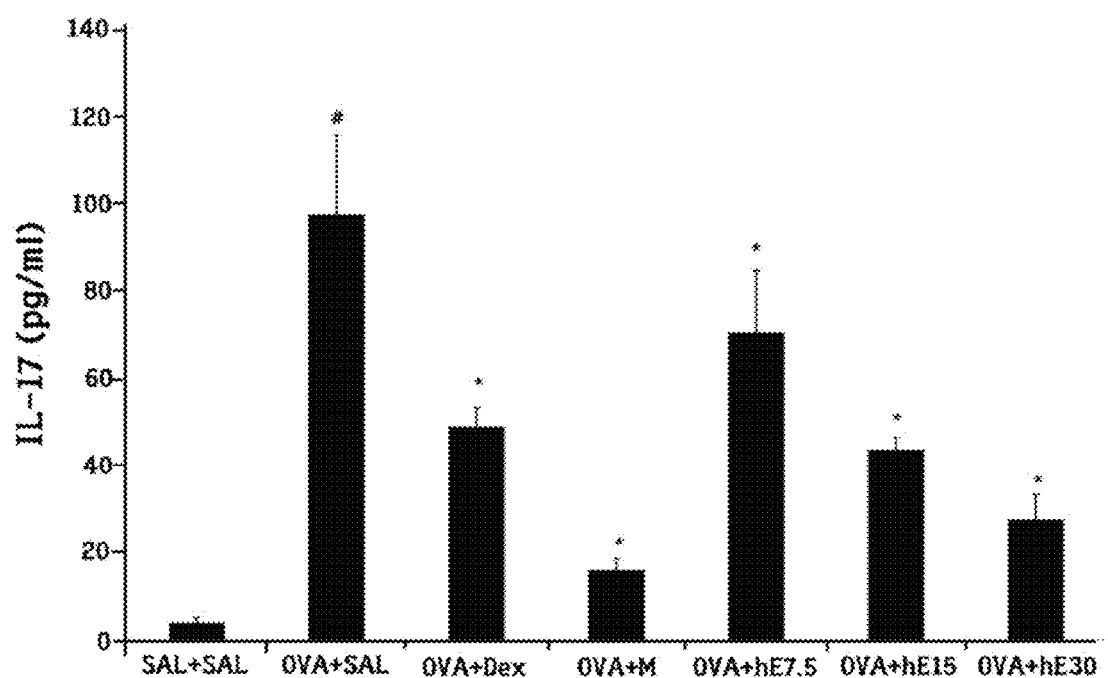

FIG. 16 is a graph illustrating IL-17 concentration in bronchoalveolar lavage fluid for each experimental group.

Figure 17:
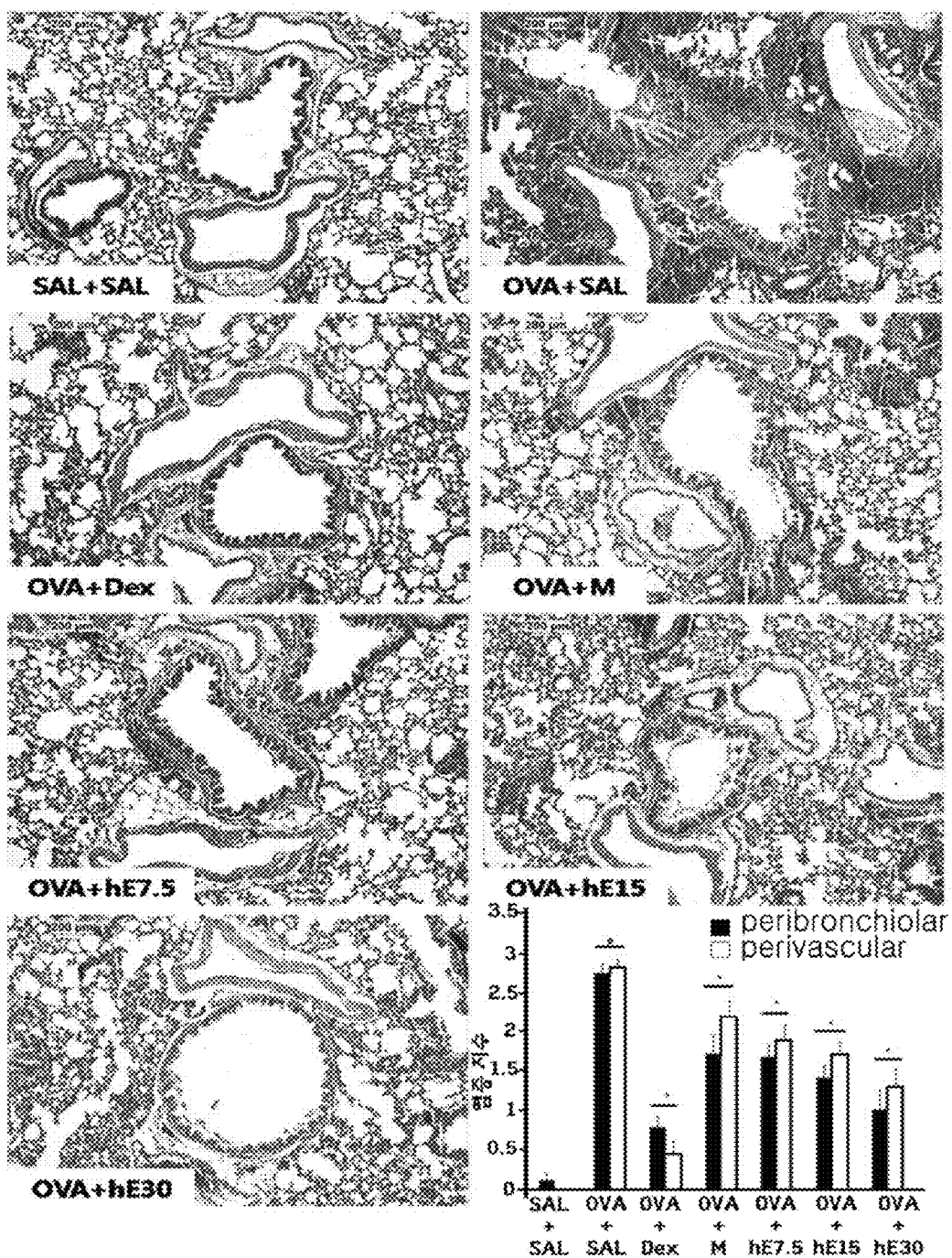

FIG. 17 is a drawing showing inflammatory cell infiltration in airway mucosa and inflammatory index for each experimental group.

Figure 18:
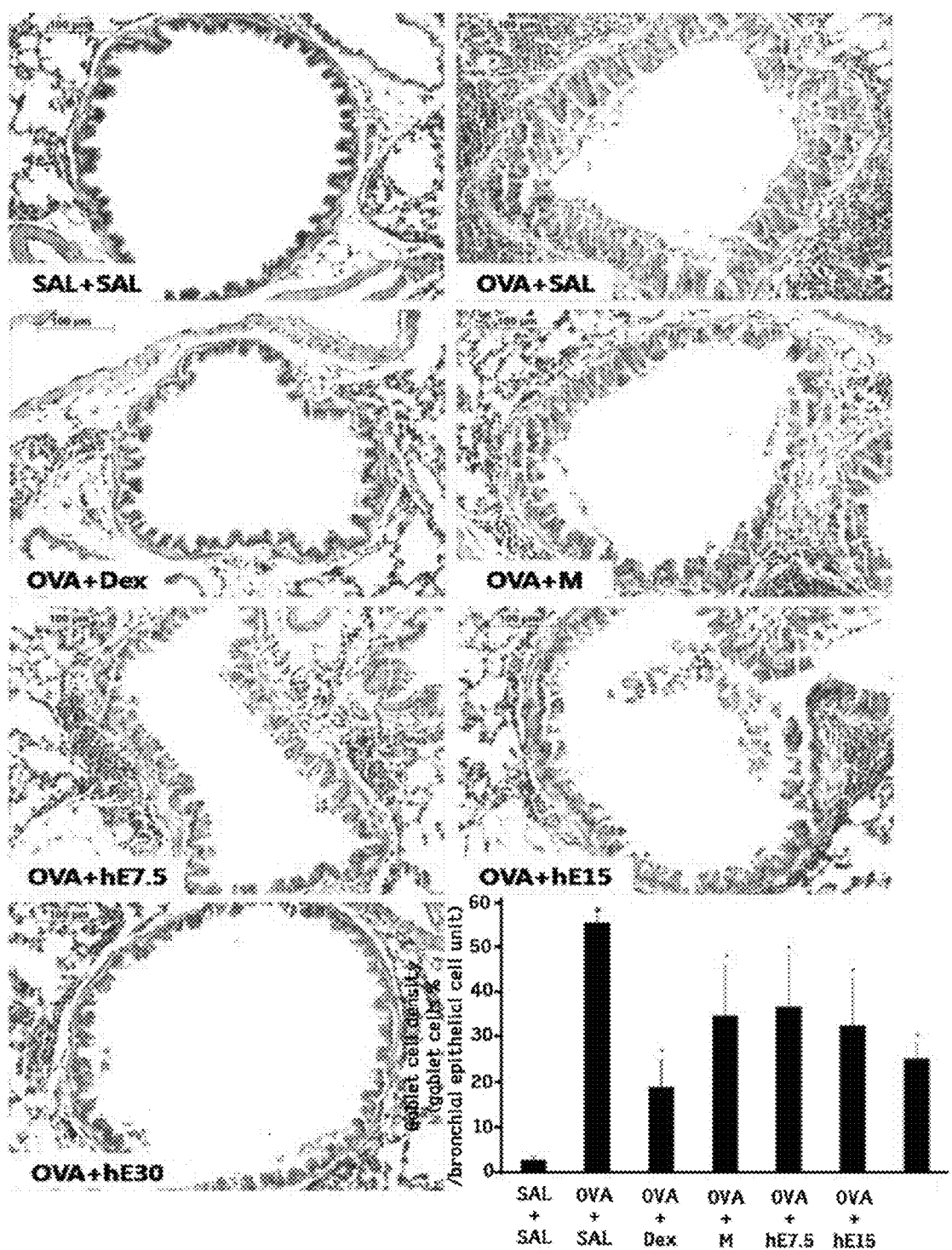

FIG. 18 is a drawing showing the ratio of goblet cells for each experimental group.

Figure 19:
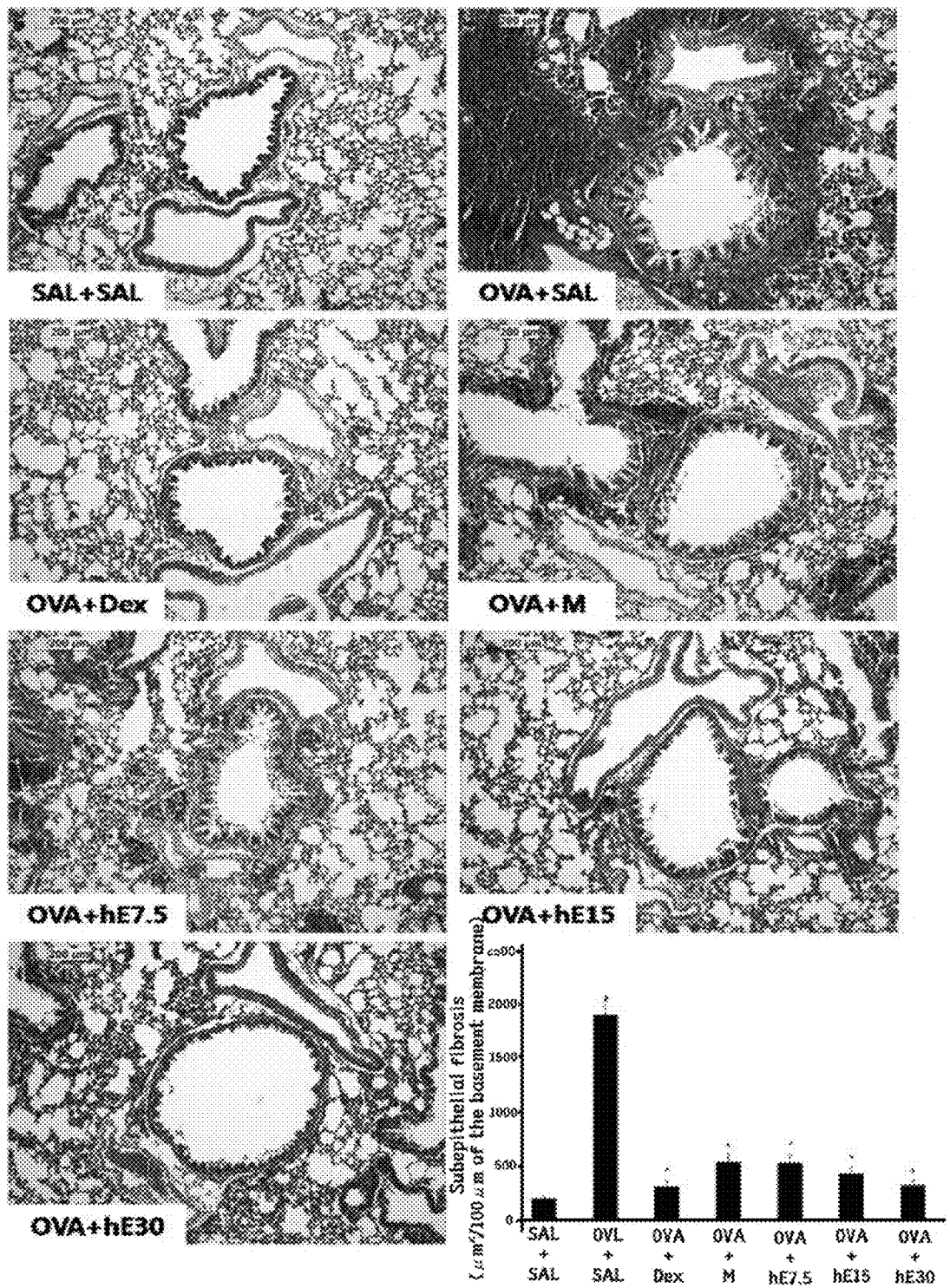

FIG. 19 is a drawing showing regions of subepithelial fibrosis for each experimental group.

FIG. 20 is a drawing showing the preparation process of homoegonol.

DESCRIPTION OF THE PREFERRED EMBODIMENTS

Terms used in the present invention will be described.

As used herein, the term "extract" has the meaning of a "crude extract" commonly used in the art, but, in a broad sense, the term includes also the following fraction.

As used herein, the term "fraction" refers to an active fraction obtained by fractionating an activity of interest in the present invention with a solvent different from a solvent used in extraction.

As used herein, the term "prevention" refers to all behavior inhibiting asthma or delaying progress of asthma by administration of a composition of the present invention.

As used herein, the terms "treatment" and "alleviation" refer to all behavior making symptoms of asthma better or changing them more favorable by the administration of the composition of the present invention.

As used herein, the term "administration" refers to providing the composition of the present invention to an individual in an arbitrary suitable way.

As used herein, the term "individual" refers to all animals having a disease of which symptoms of asthma can be made better by administering the composition of the present invention, such as humans, monkeys, dogs, goats, pigs, rats, etc.

Hereinafter, the present invention will be described in detail.

The present invention provides a pharmaceutical composition for preventing and treating asthma, the pharmaceutical compositing containing styraxlignolide A compound, an aglycone thereof, or a pharmaceutically acceptable salt thereof as an active ingredient.

The styraxlignolide A compound may be represented by the following Chemical Formula 1, but is not limited to such:

[Chemical Formula 1]

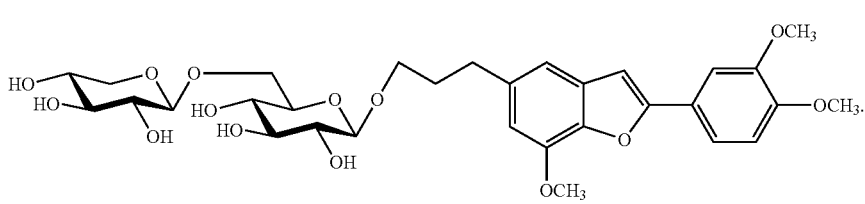

The aglycone of styraxlignolide A compound may be represented by the following Chemical Formula 2, but is not limited to such:

[Chemical Formula 2]

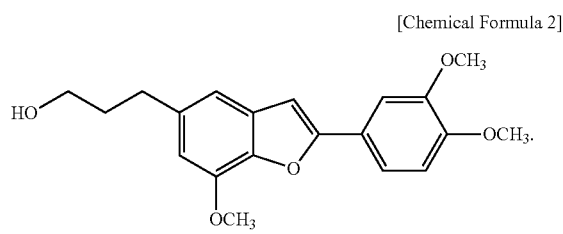 [SMILES: COc1ccc(-c2cc3cc(CCCO)cc(OC)c3o2)cc1OC]

The styraxlignolide A compound may be, but not limited to, one separated from *Styrax japonica*, and chemically synthesized one may also be used for the styraxlignolide A compound.

*Styrax japonica* may be used as a whole plant, and using stems and barks is more preferable, but the present invention is not limited to such.

The asthma may be, but not limited to, one in which airway remodeling has progressed.

The present invention includes not only the compound represented by Chemical Formula 1, the compound represented by Chemical Formula 2, or pharmaceutically acceptable salts thereof, but not only all the possible solvates and hydrates, which may be prepared therefrom.

The compound of the present invention may be used in forms of pharmaceutically acceptable salts. Useful salts are acid addition salts, which are formed by pharmaceutically acceptable free acids. Acid addition salts are obtained from inorganic acids, such as hydrochloric acid, nitric acid, phosphoric acid, sulfuric acid, hydrobromic acid, hydroiodic acid, nitrous acid or phosphorous acid, and nontoxic organic acids, such as aliphatic mono- and dicarboxylates, phenyl-substituted alkanoates, hydroxyalkanoates and alkanedioates, aromatic acids, aliphatic and aromatic sulphonic acids. Such pharmaceutically nontoxic salts include sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexane-1,6-dioate, benzoate, chlorobenzoate, methylbenzoate, dinitro benzoate, hydroxybenzoate, methoxybenzoate, phthalate, terephthalate, benzene sulfonate, toluene sulfonate, chlorobenzene sulfonate, xylene sulfonate, phenyl acetate, phenylpropionate, phenylbutyrate, citrate, lactate, β-hydroxybutyrate, glycolate, malate, tartrate, methane sulfonate, propane sulfonate, naphthalene-1-sulfonate, naphthalene-2-sulfonate or mandelate.

Acid addition salts according to the present invention may be prepared using a conventional method. For example, they may be prepared by dissolving the compound in an excess acid aqueous solution and precipitating its salt with the use of a water-miscible organic solvent, such as methanol, ethanol, acetone, or acetonitrile.

These acid addition salts may be prepared by heating the same amounts of the compound represented by Chemical Formula 1 or Chemical Formula 2 and an acid or an alcohol in water, and then evaporating this mixture to dry or by suctioning and filtering the precipitates.

Also, pharmaceutically acceptable metallic salts may be prepared by using a base. Alkali metal or alkali earth metal salts are obtained, for example, by dissolving the compound in an excessive alkali metal hydroxide or alkali earth metal hydroxide solution, filtering non-soluble compound salts, and evaporating filtrate to dry. For metallic salts, preparing sodium salts, potassium salts or calcium salts are suitable for medicine manufacture. In addition, corresponding silver salts are obtained by reacting alkali metal or alkali earth metal salts with appropriate silver salts (e.g., silver nitrate).

The styraxlignolide A compound represented by Chemical Formula 1 may be prepared by a method comprising the following steps of:

(1) extracting *Styrax japonica* with water, a lower alcohol of $C_1$ to $C_2$, or a mixture thereof;

(2) adding hexane and ethylacetate additionally to an extract in step (1) to perform systematic fractionation; and (3) carrying out a column chromatography on the remaining aqueous solution layer obtained by separating an ethylacetate layer from step (2) to obtain the compound represented by Chemical Formula 1, but the present invention is not limited to such.

Hereinafter, the preparation method of the present invention will be described step-by-step.

First, step (1) is extracting *Styrax japonica* with water, a lower alcohol of $C_1$ to $C_2$, or a mixture thereof.

In the preparation method according to the present invention, *Styrax japonica* may be any *Styrax japonica* without limitation, including cultivated, collected, or purchased *Styrax japonica*. Stems and barks of *Styrax japonica* may be used, but the present invention is not limited to such.

In the preparation method according to the present invention, the extraction solvent may be water, an alcohol, or a mixture thereof. A solvent selected from a lower alcohol of $C_1$ to $C_2$ or a mixed solvent thereof is preferable, and for the lower alcohol of $C_1$ to $C_2$, ethanol or methanol is more preferable, and methanol is most preferable, however, the present invention is not limited thereto.

The amount of the extraction solvent may be from about one-fold to about 20-fold of non-dried weight of the plant, but the present invention is not limited to such. The extraction method may be conventional methods in the art, such as hot water extraction, immersion extraction, refluxing/cooling extraction, ultrasonic extraction, etc. and extraction may be repeated from one to five times. Extraction temperature may be from about 10 to about 100° C. and room temperature is more preferable, but the present invention is not limited to such. Extraction time may be, but not limited to, from about 1 day to about 7 days, preferably 3 days.

In the preparation method according to the present invention, conventional extraction methods in the art, such as methods using an extraction equipment such as supercritical extraction, subcritical extraction, high temperature extraction, high pressure extraction, or ultrasonic extraction or methods using an adsorptive resin including XAD and HP-20 may be used to prepare the *Styrax japonica* extract, and reflux extraction with heating or room temperature extraction are preferable, but the present invention is not limited to such. Extraction may be repeated from one to five times, preferably four times, but the present invention is not limited to such.

In the preparation method according to the present invention, concentration of the obtained extract may use, but not limited to, a vacuum rotary evaporator for reduced concentration. Drying may be, but not limited to, reduced pressure drying, vacuum drying, boiling drying, spray drying, room temperature drying, or freeze drying.

Next, step (2) is adding an organic solvent to the extract obtained from step (1) to obtain a water fraction.

In the preparation method according to the present invention, the organic solvent may be, but not limited to, hexane or ethylacetate. The fraction may be any one of a hexane fraction, an ethylacetate fraction, or a water fraction, obtained by suspending the *Styrax japonica* extract in water, and then, systematically fractionating the suspended *Styrax japonica* extract with hexane and ethylacetate stepwisely, and a water fraction is the most preferable, but the present invention is not limited to such. The fraction may be obtained from the *Styrax japonica* extract by repeating the fractionation process from one to five times, preferably three times, and concentration under reduced pressure following the fractionation is preferable, but the present invention is not limited to such.

Next, step (3) is carrying out a Diaion HP-20 column chromatography and a RP C-18 column chromatography on the remaining aqueous solution layer obtained by separating an ethylacetate layer from step (2) to obtain the styraxlignolide A compound represented by Chemical Formula 1.

In the preparation method according to the present invention, carrying the chromatography may use methanol, but the present invention is not limited to such.

The therapeutically effective amount of the composition of the present invention may vary depending on many factors, for example, administration methods, target sites, a patient's condition, and the like. Thus, when the composition of the present invention is used for human bodies, the administration amount should be determined to be an appropriate amount considering both safety and effectiveness. It is also possible to estimate the amount which would be used for humans from an effective dose determined through animal experiments. Such things to consider when determining the effective amount are described in, for example, Hardman and Limbird, eds., Goodman and Gilman's The Pharmacological Basis of Therapeutics, 10th ed. (2001), Pergamon Press; and E. W. Martin ed., Remington's Pharmaceutical Sciences, 18th ed. (1990), Mack Publishing Co.

The composition of the present invention may comprise carriers, diluents, excipients, and mixtures of two or more of the foregoing that are conventionally used for biological preparations. Pharmaceutically acceptable carriers may be any one without particular limitation, provided that it is suitable for in vivo delivery of the composition. For example, compounds described in Merck Index, 13th ed., Merck & Co. Inc., saline solution, sterile water, Ringer's solution, buffered saline, dextrose solution, maltodextrin solution, glycerol, ethanol, and a mixture of one or more ingredients of the foregoing may be used, and as necessary, other conventional additives, such as antioxidants, buffer solutions, bacteristats, etc. may be added. Also, diluents, dispersants, surfactants, binders, and lubricants may be additionally added to formulate preparations for injection such as aqueous solution, suspensions, emulsions; pills; capsules; granules; or tablets. Furthermore, the composition may be formulated depending on each disease or ingredients, by an appropriate method in the art, or methods disclosed in Remington's Pharmaceutical Science (Mack Publishing Company, Easton Pa., 18th, 1990).

One or more active ingredients having the same or similar functions may be additionally contained in the composition of the present invention. The composition of the present invention may comprise about 0.0001 to about 10 weight %, preferably about 0.001 to about 1 weight %, with respect to total weight of the composition.

The composition of the present invention may be administered parenterally (for example, intravenous, subcutaneous, intraperitoneal, or topical application) or orally depending on a purposeful method. The administration dose may vary depending on body weight, age, gender, health condition, diet of a certain patient, administration period, administration method, clearance, severity of a disease, etc. The daily administration dose of the composition according to the present invention is from about 0.0001 to about 10 mg/mL, preferably from about 0.0001 to about 5 mg/mL, and it is more preferable to administer the daily dose of the composition at one time or several times a day in a divided manner.

In the present invention, stems and barks of S. japonica Sieb. Et Zucc were extracted with 100% methanol to prepare a methanol extract of S. japonica. The extract was additionally suspended in water, and hexane was added thereto to separate a hexane layer. Ethylacetate was added again to the remaining water layer to fractionate an ethylacetate layer. An active fraction was eluted from the remaining water layer using a column chromatography to separate styraxlignolide A of the present invention. Then, homoegonol which is a sugar-removed aglycone of styraxlignolide A was prepared (see FIG. 20).

To examine the inhibitory effects of the separated styraxlignolide A or homoegonol on reduction in body weight in asthma-induced mice, the present inventors measured changes in body weight of a normal control group, an asthma-induced group, asthma-therapeutic drug-administration groups for asthma-induced groups (dexamethasone or montelukast), and styraxlignolide A or homoegonol-administration groups. Consequently, the styraxlignolide A-orally administered, asthma-induced group (21.04±0.34 g) and homoegonol-orally administered, asthma-induced groups {22.10±0.13 g (7.5 mg/kg), 21.23±0.43 g (15 mg/kg), and 21.98±0.47 g (30 mg/kg)} and the dexamethasone—a synthetic steroid preparation which is used mainly for treatment of asthma or bronchial inflammation—administration group (DEXA) and the montelukast—which is conventionally used for an asthma-therapeutic agent—administration group (Monte) similarly showed body weight recovery effects close to the normal control group. Thus, styraxlignolide A or homoegonol were found to inhibit asthma-induced body weight reduction effectively (see FIG. 1 and FIG. 10).

To examine airway hyperresponsiveness caused by asthma occurrence following administration of styraxlignolide A or homoegonol, the present inventors measured the degree of airway resistance, Penh (enhanced pause) value. Consequently, while the normal control group showed a slow increase in Penh value as the concentration of methacholine increases, the asthma-induced group showed a significantly sharp increase in Penh value. Significantly reduced Penh values were found in the dexamethasone-administration group and the montelukast-administration group compared to the asthma-induced group. In the styraxlignolide A-administration groups or homoegonol-administration groups, all concentrations of methacholine treatment showed remarkably reduced Penh values compared to the comparative drug-administration groups (see FIG. 2, Table 1 and FIG. 11).

The present inventors analyzed the number of inflammatory cells in bronchoalveolar lavage fluid following administration of styraxlignolide A or homoegonol, and consequently found that the number of eosinophils was significantly reduced in the all drug-administration groups compared to the asthma-induced group, and in the styraxlignolide A or homoegonol administration groups, eosinophil infiltration was the most strongly inhibited. The numbers of total inflammatory cells were also significantly reduced in the drug-administration groups compared to the asthma-induced group (see FIG. 3, Table 4 and FIG. 14). In addition, ovalbumin-specific IgE levels in serum or bronchoalveolar lavage fluid were measured, and total serum IgE level was significantly reduced in the homoegonol-administration group compared to the asthma-induced group (see Table 2 and FIG. 12), and ovalbumin-specific IgE level in bronchoalveolar lavage fluid was significantly reduced in the styraxlignolide A or homoegonol-administration groups compared to the asthma-induced group (see FIG. 4, Table 3, and FIG. 13). Generation of TGF-β1 and IL-17 in bronchoalveolar lavage fluid was also significantly inhibited in the homoegonol-administration group (see Table 5, FIG. 15, and FIG. 16). In addition, the present inventors measured the generated amount of reactive oxygen species from bronchoalveolar lavage fluid, and found that the generated amount of reactive oxygen species in the styraxlignolide A-administration group was reduced by 27.90% compared to the asthma-induced group, and this suggested a remarkably excellent inhibitory effect on reactive oxygen species generation compared the dexamethasone or montelukast administration groups (see FIG. 5).

To examine liver toxicity of styraxlignolide A, the present inventors measured alanine aminotransferase (ALT) and aspartate aminotransferase (AST) in serum. Consequently, serum ALT and AST levels were remarkably increased in the dexamethasone-administration group compared to the asthma-induced group, and the remarkably lower level was found in the styraxlignolide A-administration group compared to the dexamethasone-administration group (see FIG. 6).

To examine effects of styraxlignolide A or homoegonol on asthma in which airway remodeling has progressed, the present inventors performed H&E staining, measured the inflammatory indexes of tissue sections, and examined inflammatory cell infiltration in mucosa, goblet cells, and subepithelial fibrosis. Consequently, it was found that in the styraxlignolide A or homoegonol administration groups, infiltration of inflammatory cells was the most strongly inhibited (see FIG. 7, Table 6 and FIG. 17), and there was the biggest drop in the ratio of goblet cells, and thus, it was found that styraxlignolide A or homoegonol inhibited mucous secretion the most strongly (see FIG. 8, Table 7, and FIG. 18). In addition, the most remarkable drop in subepithelial fibrosis was found in the styraxlignolide A or homoegonol administration groups, and it was found that styraxlignolide A or homoegonol strongly inhibited airway remodeling (see FIG. 9, Table 8, and FIG. 19).

Accordingly, styraxlignolide A or homoegonol showed more excellent inhibitory effect on airway hyperresponsiveness than dexamethasone which is currently widely used as an asthma-therapeutic agent, inhibited endobronchial infiltration of inflammatory cells, and remarkably inhibited progress of airway remodeling (bronchial epithelial cell thickening, mucous secretory cell hyperplasia, and fibrosis), but showed far lower liver toxicity than dexamethasone in an ovalbumin-caused asthma-induced animal model, and thus, styraxlignolide A compound, homoegonol, the aglycone thereof, or pharmaceutically acceptable salts thereof can be effectively used as an active ingredient for the pharmaceutical composition for preventing and treating asthma.

The present invention also provides a method for preventing asthma, the method comprising administering a pharmaceutical composition containing a pharmaceutically effective amount of styraxlignolide A compound, an aglycone thereof, or a pharmaceutically acceptable salt thereof as an active ingredient to an individual.

Furthermore, the present invention provides a method for treating asthma, the method comprising administering a pharmaceutical composition containing a pharmaceutically effective amount of styraxlignolide A compound, an aglycone thereof, or a pharmaceutically acceptable salt thereof as an active ingredient to an individual having asthma.

The pharmaceutically effective amount may be, but not limited to, from about 0.00001 to about 10 mg/kg, preferably from about 0.0001 to about 1 mg/kg. The administration dose may vary depending on body weight, age, gender, health condition, diet of a certain patient, administration period, administration method, clearance, severity of a disease, etc.

The individual may be vertebrate, preferably mammals, more preferably experimental animals, such as rats, rabbits, guinea pigs, hamsters, dogs, and cats, and most preferably anthropoids, such as chimpanzees and gorillas.

The administration method may be an oral administration or parenteral administration. For parenteral administration, intraperitoneal injection, intrarectal injection, subcutaneous injection, intravenous injection, intramuscular injection, epidural injection in uterine, intracerebrovascular injection, or intrathoracic injection may be selected.

The asthma may be, but not limited to, one in which airway remodeling has progressed.

It was found that styraxlignolide A or the aglycone thereof, homoegonol of the present invention relieved reduction in body weight and airway hyperresponsiveness, inhibited generation of reactive oxygen species in airway and endobronchial infiltration of inflammatory cells, and inhibited inflammatory cell infiltration in mucosa, the ratio of goblet cells, and subepithelial fibrosis, but showed remarkably lower liver toxicity than conventional asthma-therapeutic agents in an asthma-induced animal model, and thus, styraxlignolide A or the aglycone thereof, homoegonol of the present invention can be effectively used for the prevention or treatment of asthma.

Furthermore, the present invention provides a health food composition for preventing and alleviating asthma containing styraxlignolide A compound, an aglycone thereof, or a pharmaceutically acceptable salt thereof as an active ingredient.

The styraxlignolide A compound may be represented by the following Chemical Formula 1, but is not limited to such:

[Chemical Formula 1]

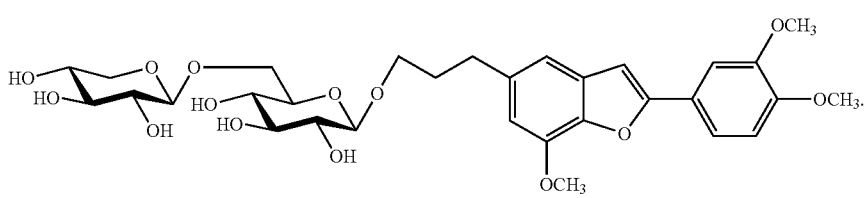

The aglycone of styraxlignolide A compound may be represented by the following Chemical Formula 2, but is not limited to such:

[Chemical Formula 2]

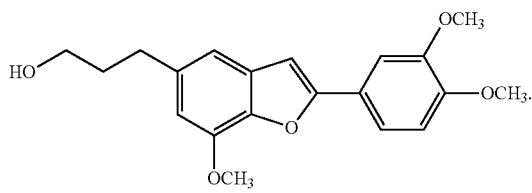

The styraxlignolide A compound may be, but not limited to, one separated from *Styrax japonica*, and chemically synthesized one may also be used for the styraxlignolide A compound.

*Styrax japonica* may be used as a whole plant, and using stems and barks is more preferable, but the present invention is not limited to such.

The asthma may be, but not limited to, one in which airway remodeling has progressed.

Styraxlignolide A compound or the aglycone thereof of the present invention may be added intactly or used with other foods or food ingredients and may be used appropriately according to conventional methods.

The health food composition of the present invention may comprise ingredients that are conventionally added for food preparation, for example, proteins, carbohydrates, fats, nutrients, and condiments.

There is no particular limitation as to the kind of food. Examples of foods to which styraxlignolide A compound or the aglycone thereof can be added include meats, sausages, breads, chocolates, candies, snacks, confectionary, pizzas, instant noodles, other noodles, gum, dairy products including ice creams, a variety of soups, beverages, teas, drinks, alcohol beverages, and vitamin complexes, etc. and include all health foods in the conventional meaning.

A health beverage composition of the present invention may comprise various flavors or natural carbohydrates, etc. as an additional ingredient like conventional beverages. The natural carbohydrate may be monosaccharides such as glucose and fructose, disaccharides such as maltose and sucrose, polysaccharides such as dextrin and cyclodextrin, and sugar alcohols such as xylitol, sorbitol, erythritol, etc. Natural sweeteners such as thaumatin and stevia extract or synthetic sweeteners such as saccharin and aspartame may used for sweeteners. The ratio of the natural carbohydrate may be generally about 0.01 to 0.04 g, preferably about 0.02 to 0.03 g based on 100 mL of the composition of the present invention.

In addition to that, styraxlignolide A compound or the aglycone thereof of the present invention may comprise various nutritional supplements, vitamins, electrolytes, flavors, colorants, pectic acid and its salt, alginic acid and its salt, organic acids, protective colloidal thickeners, pH regulating agents, stabilizers, preservatives, glycerin, alcohols, carbonizing agents used in carbonated drinks, etc. Moreover, styraxlignolide A compound or the aglycone thereof of the present invention may comprise fruit flesh for the preparation of natural fruit juices, fruit juice beverages, and vegetable beverages. These ingredients may be used alone or in combination. Although not critical, these additives are generally used in an amount from about 0.01 to about 0.1 parts by weight, based on 100 parts by weight of the composition of the present invention.

It was found that styraxlignolide A or the aglycone thereof, homoegonol of the present invention relieved reduction in body weight and airway hyperresponsiveness, inhibited generation of reactive oxygen species in airway and endobronchial infiltration of inflammatory cells, and inhibited inflammatory cell infiltration in mucosa, the ratio of goblet cells, and subepithelial fibrosis, but showed remarkably lower liver toxicity than conventional asthma-therapeutic agents in an asthma-induced animal model, and thus, styraxlignolide A or the aglycone thereof, homoegonol of the present invention can be effectively used for a health food composition for preventing or alleviating asthma.

The present invention also provides styraxlignolide A compound, an aglycone thereof, or a pharmaceutically acceptable salt thereof for using in a pharmaceutical composition for preventing and treating asthma.

Furthermore, the present invention provides styraxlignolide A compound, an aglycone thereof, or a pharmaceutically acceptable salt thereof for using in a health food composition for preventing and alleviating asthma.

The styraxlignolide A compound may be represented by the following Chemical Formula 1, but is not limited to such:

The aglycone of styraxlignolide A compound may be represented by the following Chemical Formula 2, but is not limited to such:

[Chemical Formula 2]

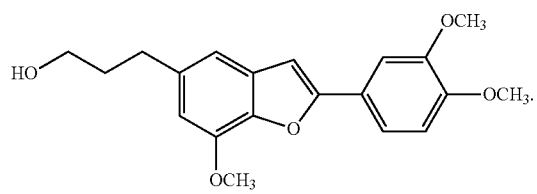

It was found that styraxlignolide A or the aglycone thereof, homoegonol of the present invention relieved reduction in body weight and airway hyperresponsiveness, inhibited generation of reactive oxygen species in airway and endobronchial infiltration of inflammatory cells, and inhibited inflammatory cell infiltration in mucosa, the ratio of goblet cells, and subepithelial fibrosis, but showed remarkably lower liver toxicity than conventional asthma-therapeutic agents in an asthma-induced animal model, and thus, styraxlignolide A or the aglycone thereof, homoegonol of the present invention can be effectively used as an active ingredient for a health food composition for preventing or alleviating asthma.

Hereinafter, the present invention will be described in more detail with reference to the following examples and preparation examples.

However, the following examples and preparation examples are provided for illustrative purposes only, and the scope of the present invention should not be limited thereto in any manner.

EXAMPLE 1

Preparation of Styraxlignolide (Styraxlignoid) A 120 kg of Stems and barks of *S. japonica* Sieb. Et Zucc., Styracaceae were collected (JeJu, Republic of Korea), and extracted four times with 5 L of methanol (MeOH). The extract was collected, and was suspended with distilled water. Then, hexane was added to the suspension, and a hexane layer was separated. Ethylacetate (EtOAc) was added to the remaining water layer, and an ethylacetate layer was separated. The resulting remaining water layer was passed through a Diaion HP-20 column, and was dissolved to separate in 8 L of distilled water, 50% MeOH, and 100% MeOH. The obtained MeOH-soluble fraction was subjected to a RP C-18 column chromatography, and was dissolved in 50% MeOH, 25% MeOH, and 100% MeOH, and styraxlignolide (styraxlignoid) A was separated.

[Chemical Formula 1]

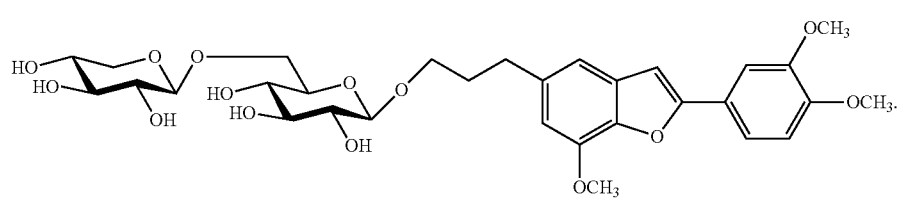

EXAMPLE 2

Preparation of Homoegonol from Styraxlignolide (Styraxlignoid) A

Homoegonol was prepared through a synthesis pathway which uses the previously reported method (See Xue Fei Yang and Ling Yi Kong, *Chinese Chemical Letters* 18, 2007, 380-382), but a novel step (step 3) is added. First, Intermediate 4 was synthesized in step 1, and Intermediate 4 and Intermediate 8 were condensed, and then, Compound 10, a precursor of trimethoxy egonol was prepared. Finally, in step 3, a carboxylic acid ester of Intermediate 10 was reduced into an alcohol to obtain the desired final Compound II (homoegonol) (FIG. 20).

EXAMPLE 3

Preparation of Bronchial Asthma Induced Experimental Animals and Treatment of Compounds To prepare bronchial asthma-induced experimental animals, six-week-old Balb/c female mice of mean weight about 20 g were used. After one week of adaptation, individuals which had no observed abnormality on a basic physical examination were targeted. 200 μL of phosphate buffered saline (PBS)(pH 7.4) in which 2 mg of aluminum hydroxide (A8222, Sigma, St. Louis, Mo.) and 20 μg of ovalbumin (A5503, Sigma, St. Louis, Mo.) were suspended was injected into the peritoneal cavity at two-week intervals to result in sensitization. On days 28 to 30 after the first intraperitoneal administration of ovalbumin, inhalation challenge was performed for 30 min with 1% ovalbumin using an ultrasonic atomizer. 24 hours after the last antigen administration, airway hyperresponsiveness was measured. After 24 hours, a lethal dose of pentobarbital (Entobar®, Hanlim Pharm Co., Ltd.) was administered, body weight measurement and bronchotomy were performed, and bronchoalveolar lavage was performed with a total 1.2 mL of physiological saline, and then, samples were collected. Experiments were proceeded with a normal control group (NC) in which mice were not administered and not challenged with ovalbumin, an asthma-induced group in which mice were administered with ovalbumin and challenged with ovalbumin inhalation, and bronchial asthma was induced, a comparative group 1 (DEXA) in which mice were orally administered with dexamethasone (3 mg/kg, PO:D4902, Sigma, St. Louis, Mo.) 1 hour prior to ovalbumin inhalation, a comparative group 2 (Monte) in which mice were orally administered with montelukast (30 mg/kg, PO) 1 hour prior to ovalbumin inhalation, and an experimental group for styraxlignolide A in which mice were orally administered with styraxlignoid A (30 mg/mL, PO) 1 hour prior to ovalbumin inhalation. Eight white mice were used for each group. Experimental groups for homoegonol were a group (hE7.5) in which animals were orally administered with 7.5 mg/kg homoegonol 1 hour prior to ovalbumin inhalation, a group (hE15) in which animals were orally administered with 15 mg/kg homoegonol 1 hour prior to ovalbumin inhalation, and a group (hE30) in which animals were orally administered with 30 mg/kg homoegonol 1 hour prior to ovalbumin inhalation, and five white mice were used for each group.

EXPERIMENTAL EXAMPLE 1

Inhibitory Effect of Styraxlignolide A on Reduction in Body Weight in Asthma-Induced Mice To determine an effect of styraxlignolide A on reduction in body weight in asthma-induced mice, body weight of each mouse prepared in Example 2 was measured. For statistical analyses for all measurements, means and standard errors (mean±S.E.) according to a number of variables were calculated, and comparison between each group was analyzed by performing a Mann-whitney U test using SPSS 10.0. Statically significance was accepted at $p<0.05$.

Figure 1:
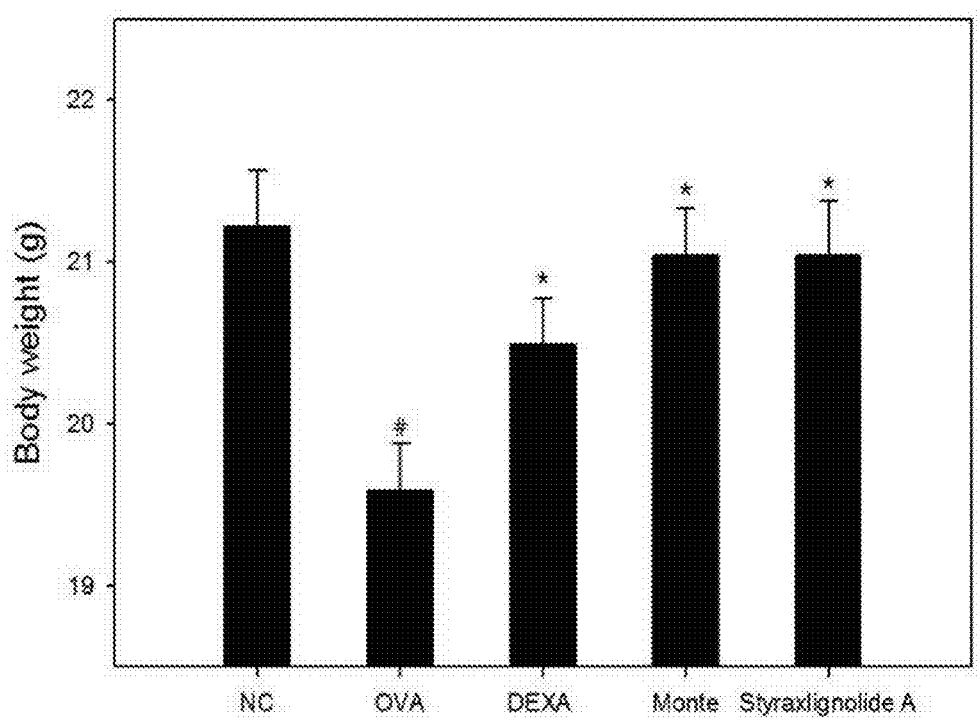
FIG. 1 is a graph illustrating the measured body weights for a normal control group (NC), an asthma-induced group (OVA), a Dexamethasone-administered asthma-induced group (DEXA), a montelukast-administered asthma-induced group (Monte), and a styraxlignolide A-administered asthma-induced group (Styraxlignolide A)(hereinafter, #: statistically significant compared to the normal control group (NC) ($p<0.05$), *: statistically significant compared to the asthma-induced group (OVA)($p<0.05$).

Consequently, as shown in FIG. 1, while the bodyweight of the normal control group was 21.22±0.31 g, the body weight of the asthma-induced group (OVA) was 19.59±0.27 g, and was reduced remarkably. However, the body weight of the comparative group 1 (DEXA) which is the dexamethasone-administration group was 20.49±0.29 g, and the body weight of the comparative group 2 (Monte) which is the montelukast-administration group was 21.04±0.30 g, and the body weight of the styraxlignolide A-administration group was 21.04±0.34 g. From the results, it was found that the styraxlignolide A-administration group exhibited a similar body weight recovery effect to the conventional anti-asthma drug-administration groups (FIG. 1).

EXPERIMENTAL EXAMPLE 2

Inhibitory Effect of Styraxlignolide A on Airway Hyperresponsiveness Caused by Asthma Occurrence The effect of styraxlignolide A on airway hyperresponsiveness caused by asthma occurrence was examined by measuring airway resistance with one chamber plethysmography (All medicus, Seoul, Republic of Korea) and degree of airway resistance was assessed by measuring Penh (enhanced pause) values. The baseline value was measured under a normal respiratory condition, and then, PBS was inhaled using an ultrasonic atomizer for 3 min, and Penh values were measured over 3 min. Then, increasing doses of histamine methacholine (12, 25, and 50 mg/mL concentrations; A2251, Sigma, St. Louis, Mo.) which is used in general methods for diagnosis of bronchial asthma were inhaled and Penh values were measured. Penh value is shown in the following Equation 1, and the resulting Penh value was expressed as a percent increase in Penh after inhalation of each concentration of methacholine. The baseline Penh (saline challenge) was expressed as 100%.

$$Penh = \left(\frac{Te}{RT-1}\right) \times \frac{PEF}{PIF} \qquad \text{[Equation 1]}$$

Te: expiratory time (sec), the time from inspiration to the next inspiration

Figure 2:
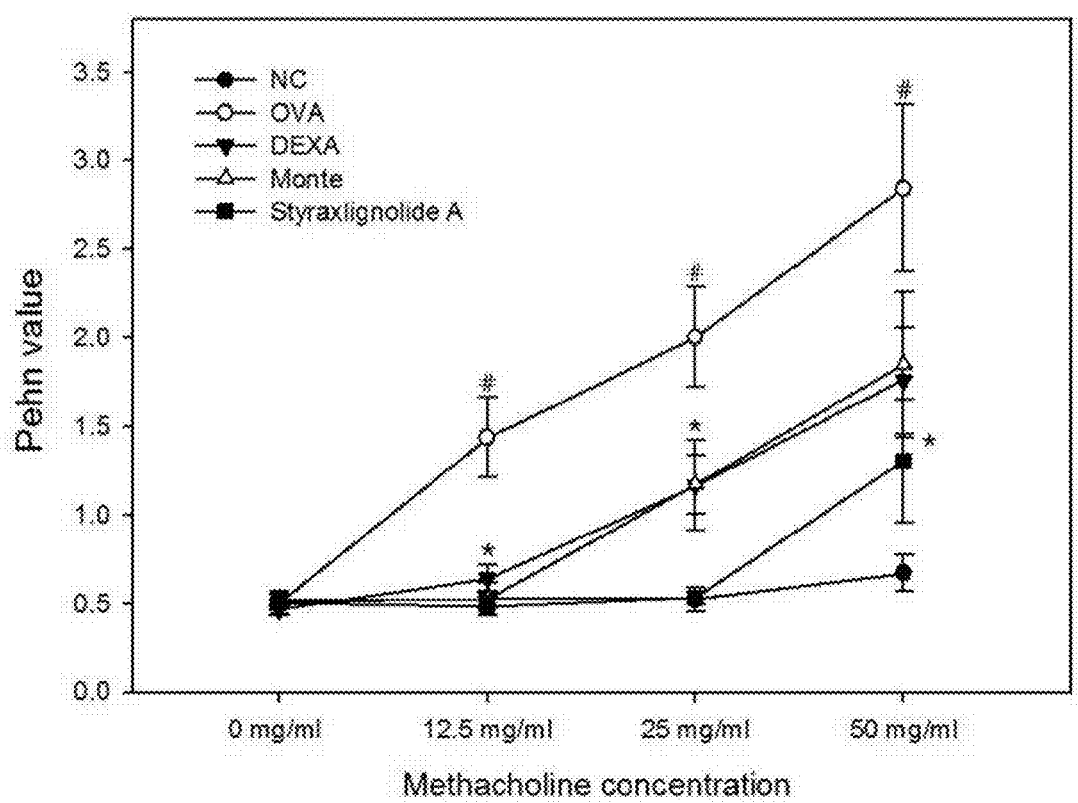
FIG. 2 is a graph illustrating airway hyperresponsiveness for each experimental group as Penh (enhanced pause) value.

RT: relaxation time, the elapsed time between the beginning of the expiration and the moment when the remaining 30% of the tidal volume has been reached during expiration PEF: Peak expiration flow PIF: Peak inspiration flow Consequently, as shown in FIG. 2, while the normal control group (NC) showed a slow increase in Penh value as the concentration of methacholine increases, the asthma-induced group (OVA) showed a significantly sharp increase in Penh value. Significantly reduced Penh values were found in the comparative group 1 (DEXA) and the comparative group 2 (Monte) compared to the asthma-induced group. In the styraxlignolide A-administration groups, all concentrations of 12.5, 25, or 50 mg/mL of methacholine showed reduced Penh values compared to the comparative groups (FIG. 2).

EXPERIMENTAL EXAMPLE 3

Inhibitory Effect of Styraxlignolide A on Inflammatory Cells in Bronchoalveolar Lavage Fluid Bronchoalveolar lavage fluid was collected from individuals of each experimental group in <Example 2> and right after the collection, fluid was stained with trypan blue. The number of total cells except dead cells was calculated using a hemocytometer. Then, Diff-Quick staining (Sysmex, Swizerland) was performed after smear preparation with Cytospin II, and eosinophils and other inflammatory cells were differentially counted.

Figure 3:
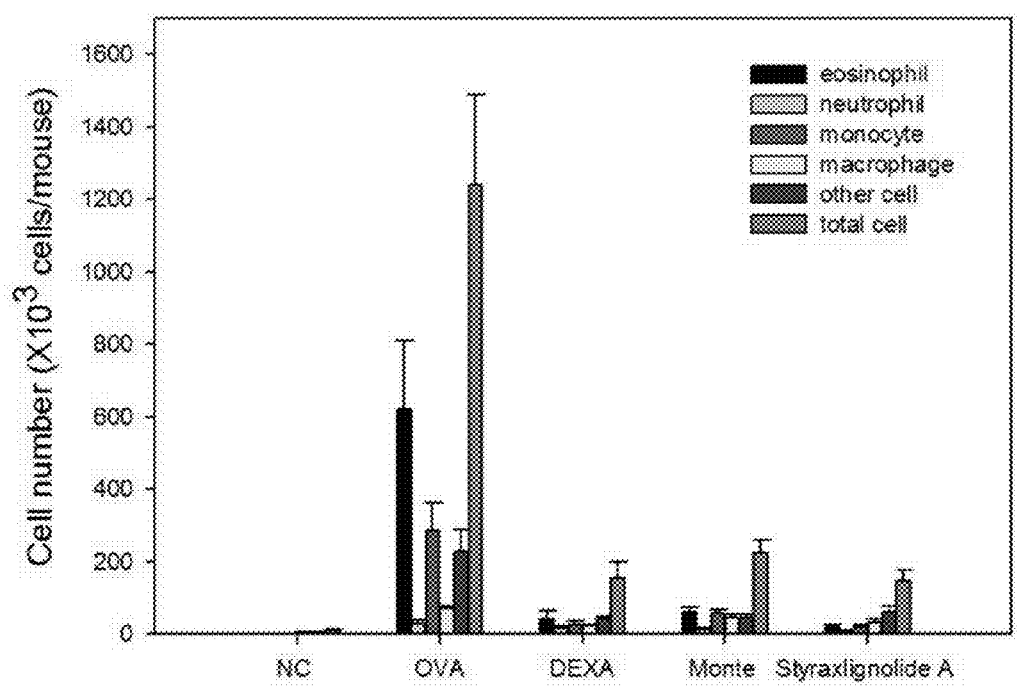
FIG. 3 is a graph illustrating the number of inflammatory cells in bronchoalveolar lavage fluid for each experimental group.

Consequently, as shown in FIG. 3, the numbers of eosinophils were measured as 0±0 in the normal control group (NC), 622.55±74.18 in the asthma-induced group (OVA), 41.88±9.08 in the comparative group 1 (DEXA), 60.67±6.58 in the comparative group 2 (Monte), and 20.77±2.34 in the styraxlignolide A-administration group. The numbers of eosinophils were significantly reduced in drug-administration groups compared to the asthma-induced group, and in particular, infiltration of eosinophils was strongly inhibited in the styraxlignolide A-administration group. The numbers of total inflammatory cells including other inflammatory cells were measured as 10.15±2.05 in the normal control group, 1238.65±101.01 in the asthma-induced group, 153.48±19.69 in the comparative group 1, 193.29±19.99 in the comparative group 2, and 147.83±12.61 in the styraxlignolide A-administration group, and the numbers of total inflammatory cells were significantly reduced in the drug-administration groups compared to the asthma-induced group (FIG. 3).

EXPERIMENTAL EXAMPLE 4

Inhibitory Effect of Styraxlignolide A on Ovalbumin-specific IgE in Bronchoalveolar Lavage Fluid To measure serum and bronchoalveolar lavage fluid ovalbumin-specific IgE levels caused by administration of styraxlignolide A, an immunoenzyme technique was used. 20 μg/mL of ovalbumin was dissolved in a 0.1 M NAHCO$_3$ buffer (pH 8.3), and was placed into a 96-well flat bottom ELISA plate to be coated at 4° C. overnight. Non-specific binding was blocked with PBS containing 1% bovine serum albumin, and a serum sample was diluted 1:400 and was allowed to react at room temperature for 2 hours. Then, the plate was washed well, and anti-mouse IgE monoclonal antibody was diluted 1:300 and was allowed to react for 2 hours. Then, HRP-conjugated goat anti-rat IgG polyclonal antibody which was coupled to peroxidase was diluted 1:4000 and was allowed to react at room temperature for 1 hour, and then, was washed. For color development, 3,3',5,5'-tetramethylbezidine substrate was allowed to react, and the spectroscopic absorbance was measured at 650 nm.

Consequently, as shown in FIG. 4, serum ovalbumin-specific IgE level was reduced in the styraxlignolide A-administration group (382 ±60.60 ng/mL) compared to the asthma-induced group (462±79.82 ng/mL), but the difference was not significant. Ovalbumin-specific IgE level in bronchoalveolar lavage fluid was significantly reduced in the styraxlignolide A-administration group (15.4±2.18 ng/mL) compared to the asthma-induced group (26.5±2.96 ng/mL)(FIG. 4).

EXPERIMENTAL EXAMPLE 5

Inhibitory Effect of Styraxlignolide A on Reactive Oxygen Species Generation

To measure the amount of generated reactive oxygen species caused by administration of styraxlignolide A, some bronchoalveolar lavage fluid of each individual in <Example 2> was washed with PBS, and 10 μM 2,7-dichlorofluorescein diacetate (35845, Sigma, St. Louis, Mo.) was added thereto and bronchoalveolar lavage fluid was allowed to stand still in a room temperature dark room for 10 min, and the amount of generated reactive oxygen species was measured by a spectrofluorometer (Ex=480 nm, Em=522 nm).

Consequently, as shown in FIG. 5, the generated amount of reactive oxygen species in the styraxlignolide A-administration group was reduced by 27.90% compared to the asthma-induced group, and the styraxlignolide A-administration group showed an excellent inhibitory effect on reactive oxygen species generation compared the comparative groups 1 and 2 (FIG. 5).

EXPERIMENTAL EXAMPLE 6

Assessment of Liver Toxicity of Styraxlignolide A

To examine liver toxicity of styraxlignolide A, a commercially available ELISA kit (BECKMAN Coulter, Inc., Fullerton, Calif., USA) was used to measure alanine aminotransferase (ALT) and aspartate aminotransferase (AST) in serum.

Consequently, as shown in FIG. 6, serum ALT and AST levels were significantly increased in the comparative group 1 (DEXA)(ALT: 274.67±12.12 IU/L, AST: 369.33±31.27 IU/L) compared to the asthma-induced group (ALT: 132±19.25 IU/L, AST: 235.33±22.40 IU/L). Meanwhile, the significantly lower level was found in the comparative group 2 (Monte)(ALT: 122.50±14.94 IU/L, AST: 205.00±27.17 IU/L) and the styraxlignolide A-administration group (ALT: 168.67±15.56 IU/L, AST: 245.33±12.87 IU/L) compared to the comparative group 1 (FIG. 6).

EXPERIMENTAL EXAMPLE 7

Inhibitory Effect of Styraxlignolide A on Airway Remodeling

<7-1> Inhibition of Infiltration of Inflammatory Cells in the Airway Mucosa

Lungs removed from each individual were subjected to conventional formalin fixation and paraffin embedding, and permanent section slides of 4 μm thickness were prepared, and hematoxylin and eosin (H&E) staining was performed. After H&E staining, inflammatory index was measured from random five regions per section slide of each individual to calculate the mean value. Assessments were as follows: inflammatory index 0 is for the case that inflammatory cells are not observed around the bronchus; inflammatory index 1 is for the case that inflammatory cells are intermittently observed; inflammatory index 2 is for the case that thin inflammatory cell layers of one to two or three layers are observed around most of the bronchus; inflammatory index 3 is for the case that inflammatory cell layers of two or three to five or less layers are observed around most of the bronchus; and inflammatory index 4 is for the case that thick inflammatory cell layers of five or more layers are observed around most of the bronchus.

Consequently, as shown in FIG. 7, in the asthma-induced group, many inflammatory cells including eosinophils were infiltrated around the bronchiole and hyperplastic epithelial cells and thickened bronchial smooth muscles were also found. Meanwhile, in the drug-administration groups, infiltration of inflammatory cells was significantly reduced. When infiltration of inflammatory cells was rated, peribronchiolar inflammatory indexes were 4.00±0.00 in the asthma-induced group, 1.46±0.26 in the comparative group 1 (DEXA), 2.00±0.23 in the comparative group 2 (Monte), 1.17±0.2 in the styraxlignolide A-administration group, and all these inflammatory indexes were significantly reduced compared to the asthma-induced group. In particular, it was found that in the styraxlignolide A-administration group, infiltration of inflammatory cells was the most strongly inhibited (FIG. 7).

<7-2> Inhibition of Goblet Cells

Lungs removed from each individual were subjected to conventional formalin fixation and paraffin embedding, and permanent section slides of 4 μm thickness were prepared, and periodic acid Schiff (PAS) staining was performed to determine goblet cells. Proliferation of goblet cells was assessed by measuring the ratio of goblet cells to bronchial epithelial cells.

Consequently, as shown in FIG. 8, while the ratio of goblet cells to bronchiolar epithelial cells was 0.65±0.91% in the normal control group, it was increased to 57.52±6.19% in the asthma-induced group, and it was significantly decreased in the comparative group 1 (DEXA)(34.96±6.86%), the comparative group 2 (Monte)(37.05±7.19%), and the styraxlignolide A-administration group (29.52±8.02%), and the biggest drop was found in the styraxlignolide A-administration group. From this, it was found that styraxlignolide A strongly inhibited mucous secretion (FIG. 8).

<7-3> Inhibition of Fibrosis in Subsegmental Bronchi

To measure degree of fibrosis in subsegmental bronchi, lungs removed from each individual were subjected to conventional formalin fixation and paraffin embedding, and permanent section slides of 4 μm thickness were prepared, and Masson's trichrome staining was performed to measure an area of subepithelial staining extracellular matrix. Then, an area of a fibrosis stained region per 100 μm of a basement membrane perimeter was calculated. All measurements were performed using a computerized image analyzer program.

Consequently, as shown in FIG. 9, the area of a fibrosis stained region per 100 μm of a basement membrane perimeter was 371.25±100.39 μm$^2$ in the normal control group. In the asthma-induced group, it was 2173.88±275.27 μm$^2$, which was increased by about 7 times, compared to the normal control group. Fibrosis was significantly decreased in all of the comparative group 1 (DEXA)(639.59±106.96 μm$^2$), the comparative group 2 (Monte)(991.75±108.35 μm$^2$), and the styraxlignolide A-administration group (495.69±98.62 μm$^2$), and the biggest drop was found in the styraxlignolide A-administration group. From this, it was found that styraxlignolide A strongly inhibited airway remodeling (FIG. 9).

EXPERIMENTAL EXAMPLE 8

Inhibitory Effect of Homoegonol on Reduction in Body Weight in Asthma-Induced Mice To determine an effect of homoegonol on reduction in body weight in asthma-induced mice, body weight of each mouse prepared in Example 2 was measured. For statistical analyses for all measurements, means and standard errors (mean±S.E.) according to a number of variables were calculated, and comparison between each group was analyzed by performing a Mann-whitney U test using SPSS 10.0. Statically significance was accepted at $p<0.05$.

Consequently, as shown in FIG. 10, while the bodyweight of the normal control group was 21.96±0.25 g, the body weight of the asthma-induced group was 18.52±0.45 g, and was reduced remarkably. However, the body weight for each group was 19.98±0.39 g (the comparative group 1 (DEXA)), 21.08±0.57 g (the comparative group 2 (Monte)), 22.10±0.13 g (the 7.5 mg/kg of homoegonol-orally administered group), 21.23±0.43 g (the 15 mg/kg of homoegonol-orally administered group), and 21.98±0.47 g of the 30 mg/kg of homoegonol-orally administered group). From the results, it was found that the drug-administration groups except the comparative group 1 (DEXA) showed similar body weight recovery to the normal control group (FIG. 10).

EXPERIMENTAL EXAMPLE 9

Inhibitory Effect of Homoegonol on Airway Hyperresponsiveness Caused by Asthma Occurrence To examine the effect of homoegonol on airway hyperresponsiveness caused by asthma occurrence, Penh value was measured according to the method in <Experimental Example 2>. Consequently, as shown in Table 1 and FIG. 11, while the normal control group showed a slow increase in Penh value as the concentration of methacholine increases, the asthma-induced group showed a significantly sharp increase in Penh value. Meanwhile, Penh values were significantly reduced in the comparative group 1 (DEXA), the comparative group 2 (Monte), and the homoegonol-administered groups (hE7.5, hE15 and hE30) compared to the asthma-induced group regardless of the concentration of methacholine, and there was a tendency to more decrease in Penh values in those groups as the homoegonol treatment concentration increases. In addition, when a higher, rather than lower, concentration of methacholine was inhaled, there was a clear difference.

TABLE 1

| Groups | Penh values | | | |
|---|---|---|---|---|
| | 0 mg/ml | 12.5 mg/ml | 25 mg/ml | 50 mg/ml |
| hE7.5 | 0.6003 ± 0.0500 | 1.1399 ± 0.1279 | 1.4067 ± 0.1279 | 1.4317 ± 0.2094 |
| hE15 | 0.4538 ± 0.0376 | 0.7989 ± 0.0736 | 1.0243 ± 0.1881 | 1.0918 ± 0.1914 |
| hE30 | 0.4736 ± 0.0420 | 0.6516 ± 0.0914 | 0.9515 ± 0.1268 | 1.0576 ± 0.1582 |
| Normal Control (NC) | 0.3231 ± 0.0351 | 0.3897 ± 0.0501 | 0.5210 ± 0.0710 | 0.6763 ± 0.0678 |
| Asthma-induced (OVA) | 0.9621 ± 0.1292 | 4.5805 ± 0.4980 | 7.2499 ± 0.5919 | 8.8944 ± 0.9386 |
| Comparative 1 (DEXA) | 0.4407 ± 0.0422 | 0.7768 ± 0.1475 | 0.8900 ± 0.1619 | 1.1036 ± 0.4048 |
| Comparative 2 (Monte) | 0.6071 ± 0.0618 | 1.2979 ± 0.1537 | 1.4748 ± 0.1639 | 2.3069 ± 0.4225 |

EXPERIMENTAL EXAMPLE 10

Measurement of Homoegonol-Induced IgE Levels in Serum and Bronchoalveolar Lavage Fluid To measure IgE levels which are correlated with severity of asthma to examine the effect of homoegonol on asthma, IgE levels in serum and bronchoalveolar lavage fluid were measured according to the method in <Experimental Example 4>.

Consequently, as shown in the following Table 2 and FIG. 12, serum IgE levels in the homoegonol-administration groups of the present invention were measured to be 19.22±4.9287 μg/mL (hE7.5), 10.74±3.4612 μg/mL (hE15), and 8.14±5.9682 μg/mL (hE30) compared to the asthma-induced group (OVA)(11.85±2.6994 μg/mL), and IgE antibody in serum was found to decrease significantly with homoegonol concentration. Also, as shown in the following Table 3 and FIG. 13, IgE antibody levels in bronchoalveolar lavage fluid in the homoegonol-administration groups were measured to be 65.5957±11.6656 ng/mL (hE7.5), 48.4894±4.1926 ng/mL (hE15), and 23.8085±3.3515 ng/mL (hE30) compared to the asthma-induced group (146.5745±18.7560 ng/mL), and IgE antibody in bronchoalveolar lavage fluid was found to decrease significantly with homoegonol concentration.

TABLE 2

|  | Total serum IgE level (μg/ml) |
| --- | --- |
| hE7.5 | 10.34 ± 6.0548 |
| hE15 | 9.94 ± 5.0656 |
| hE30 | 8.62 ± 2.4844 |
| Normal Control (NC) | 5.98 ± 0.4775 |
| Asthma-induced (OVA) | 20.58 ± 3.3923 |
| Comparative 1 (DEXA) | 9.14 ± 2.0591 |
| Comparative 2 (Monte) | 16.22 ± 2.6329 |

TABLE 3

|  | Total IgE level in bronchoalveolar lavage fluid (ng/ml) |
| --- | --- |
| hE7.5 | 65.5957 ± 11.6656 |
| hE15 | 48.4894 ± 4.1926 |
| hE30 | 23.8085 ± 3.3515 |
| Normal Control (NC) | 7.2979 ± 2.6622 |
| Asthma-induced (OVA) | 146.5745 ± 18.7560 |
| Comparative 1 (DEXA) | 24.3617 ± 4.8149 |
| Comparative 2 (Monte) | 104.7447 ± 9.7295 |

EXPERIMENTAL EXAMPLE 11

Inhibitory Effect of Homoegonol on Inflammatory Cells in Bronchoalveolar Lavage Fluid To examine the effect of homoegonol on asthma, variation in the numbers of asthma-related inflammatory cells was measured according to the method in <Experimental Example 3>.

Consequently, as shown in the following Table 4 and FIG. 14, the numbers of total inflammatory cells were measured to be 6.68±0.7626 in the normal control group, 225.00±23.6323 in the asthma-induced group, 20.04±4.7744 in the comparative group 1 (DEXA), 67.96±15.0532 in the comparative group 2 (Monte), and 42.80±7.2060 (hE7.5), 39.72±4.4400 (hE15) and 33.88±8.1589 (hE30) in the homoegonol-administration groups, respectively, and inflammatory cells were significantly reduced in the all homoegonol-administration groups compared to the asthma-induced group. In particular, the numbers of eosinophils, the cells which infiltrate into tissues, and are involved in cell-mediated immunity, are distributed across cells, spleen, respiratory organs, and so on, and contain inflammatory proteins, and thus, are known to play an important role in the occurrence of asthma, were measured to be 0.00±0.00 in the normal control group, 108.88±14.09 in the asthma-induced group, 1.32±0.49 in the comparative group 1, 19.12±9.17 in the comparative group 2, and 12.80±2.50 (hE7.5), 6.32±0.86 (hE15), and 5.48±2.02 (hE30) in the homoegonol-administration groups, respectively, and the numbers of eosinophils were significantly reduced in the all homoegonol-administration groups compared to the asthma-induced group.

TABLE 4

| | Number of cells (×10$^3$ cells/mouse) | | |
| --- | --- | --- | --- |
| Groups | Eosinophils | Other inflammatory cells | Total inflammatory cells |
| hE7.5 | 12.80 ± 2.50 | 33.40 ± 2.3467 | 42.80 ± 7.2060 |
| hE15 | 6.32 ± 0.86 | 30.00 ± 2.8267 | 39.72 ± 4.4400 |
| hE30 | 5.48 ± 2.02 | 28.4 ± 3.1739 | 33.88 ± 8.1589 |
| Normal Control (NC) | 0.00 ± 0.00 | 6.68 ± 0.7626 | 6.68 ± 0.7626 |
| Asthma-induced (OVA) | 108.88 ± 14.09 | 116.12 ± 5.9846 | 225.00 ± 23.6323 |
| Comparative 1 (DEXA) | 1.32 ± 0.49 | 18.72 ± 2.2919 | 20.04 ± 4.7744 |
| Comparative 2 (Monte) | 19.12 ± 9.17 | 48.84 ± 3.7377 | 67.96 ± 15.0532 |

EXPERIMENTAL EXAMPLE 12

Inhibitory Effect of Homoegonol on TGF-β1 and IL-17 in Bronchoalveolar Lavage Fluid To examine the effect of homoegonol on airway remodeling, generation of TGF-β1 and IL-17 in bronchoalveolar lavage fluid was measured.

Consequently, as shown in the following Table 5, FIG. 15, and FIG. 16, the homoegonol-administration groups significantly inhibited TGF-β1 and IL-17 in bronchoalveolar lavage fluid compared to the asthma-induced group.

TABLE 5

|  | TGF-β1 concentrations in bronchoalveolar lavage fluid (pg/ml) | IL-17 concentrations in bronchoalveolar lavage fluid (pg/ml) |
| --- | --- | --- |
| hE7.5 | 216.1875 ± 13.5904 | 70.3409 ± 14.2912 |
| hE15 | 190.4375 ± 13.0702 | 43.5682 ± 2.9102 |
| hE30 | 186.8125 ± 6.4551 | 27.3863 ± 5.7881 |
| Normal Control (NC) | 50.6875 ± 44.8720 | 3.8863 ± 1.2613 |
| Asthma-induced (OVA) | 376.8125 ± 24.2240 | 97.5682 ± 18.1885 |
| Comparative 1 (DEXA) | 159.2813 ± 12.9548 | 48.8409 ± 4.3738 |
| Comparative 2 (Monte) | 215.9375 ± 13.4334 | 15.8409 ± 2.5686 |

EXPERIMENTAL EXAMPLE 12

Histopathological Analysis Following Homoegonol Administration

To examine the effect of homoegonol on asthma, lungs of which bronchoalveolar lavage was not performed were removed, and histopathological assessment was performed according to the method in <Experimental Example 7-1>. Since infiltration of inflammatory cells which are comprised of eosinophils, neutrophils, and macrophages are observed in an antigen-aroused bronchus, the present inventors tried to detect inflammatory cell infiltration.

Consequently, many inflammatory cells including eosinophils were infiltrated around bronchioles in the asthma-induced group, and hyperplastic epithelial cells and thickened bronchial smooth muscles were also identified. Meanwhile, as shown in Table 6 and FIG. 17, inflammatory cell infiltration was remarkably reduced in the drug-administration groups. When inflammatory cell infiltration was rated, peribronchiolar inflammatory indexes were 2.75±0.1083 in the asthma-induced group, 0.78±0.1315 in the comparative group 1 (DEXA), 1.70±0.2470 in the comparative group 2 (Monte), and 1.67±0.1491 (hE7.5), 1.40±0.1549 (hE15), and 1.00±0.2449 (hE30) in the homoegonol-administration groups, respectively, and all these inflammatory indexes were significantly reduced compared to the asthma-induced group. In addition, perivascular inflammatory indexes were 32.81±0.0976 in the asthma-induced group, 0.44±0.1571 in the comparative group 1 (DEXA), 2.20±0.1897 in the comparative group 2 (Monte), and 1.89±0.1791 (hE7.5), 1.70±0.1449 (hE15), and 1.30±0.2025 (hE30) in the homoegonol-administration groups, respectively, and all these inflammatory indexes were significantly reduced compared to the asthma-induced group.

TABLE 6

| | Inflammatory index | |
|---|---|---|
| | peribronchiolar | perivascular |
| hE7.5 | 1.67 ± 0.1491 | 1.89 ± 0.1791 |
| hE15 | 1.40 ± 0.1549 | 1.70 ± 0.1449 |
| hE30 | 1.00 ± 0.2449 | 1.30 ± 0.2025 |
| Normal Control (NC) | 0.10 ± 0.0949 | 0.00 ± 0.00 |
| Asthma-induced (OVA) | 2.75 ± 0.1083 | 2.81 ± 0.0976 |
| Comparative 1 (DEXA) | 0.78 ± 0.1315 | 0.44 ± 0.1571 |
| Comparative 2 (Monte) | 1.70 ± 0.2470 | 2.20 ± 0.1897 |

EXPERIMENTAL EXAMPLE 13

Inhibitory Effect of Homoegonol on Goblet cells

In accordance with the method in <Experimental Example 7-2>, the ratio of goblet cells which were determined by periodic acid-Schiff staining to bronchial epithelial cells were measured to assess proliferation of goblet cells.

Consequently, as shown in Table 7 and FIG. 18, while the ratio of goblet cells to bronchiolar epithelial cells was 2.7741±0.7381% in the normal control group, it was increased to 55.5196±1.3706% in the asthma-induced group, and it was decreased to 18.7828±5.9397% in the comparative group 1 (DEXA), 34.6476±11.5492% the comparative group 2 (Monte), and 36.5600±11.5613% (hE7.5), 32.4109±10.8037% (hE15), and 25.0956±3.4033% (hE30) in the homoegonol-administration groups, and all the ratios were significantly reduced compared to the asthma-induced group.

TABLE 7

| | Goblet cells %/bronchial epithelial cell unit |
|---|---|
| hE7.5 | 36.5600 ± 11.5613 |
| hE15 | 32.4109 ± 10.8037 |
| hE30 | 25.0956 ± 3.4033 |
| Normal Control (NC) | 2.7741 ± 0.7381 |
| Asthma-induced (OVA) | 55.5196 ± 1.3706 |
| Comparative 1 (DEXA) | 18.7828 ± 5.9397 |
| Comparative 2 (Monte) | 34.6476 ± 11.5492 |

EXPERIMENTAL EXAMPLE 14

Inhibitory Effect of Homoegonol on Fibrosis in Subsegmental Bronchi

To measure degree of fibrosis in subsegmental bronchi in accordance with the method in <Example 7-3>, Masson's trichrome staining was performed to measure an area of subepithelial staining extracellular matrix. Then, an area of a fibrosis stained region per 100 μm of a basement membrane perimeter was calculated.

Consequently, as shown in Table 8 and FIG. 19, the area of a fibrosis stained region per 100 μm of a basement membrane perimeter was 195.95±19.0464 μm$^2$ in the normal control group. In the asthma-induced group, it was 1907.34±85.3287 μm$^2$, which was increased by about 10 times, compared to the normal control group. Fibrosis was measured to be 308.77±49.0266 μm$^2$ in the comparative group 1 (DEXA), 537.98±72.4581 μm$^2$ in the comparative group 2 (Monte), and 527.25±71.3953 μm$^2$ (hE7.5), 425.64±64.6798 μm$^2$ (hE15), and 320.99±46.2236 μm$^2$ (hE7.5) in the homoegonol-administration groups, respectively, and fibrosis was significantly decreased in the all drug-administration groups compared to the asthma-induced group.

TABLE 8

| | μm$^2$/100 μm of basement membrane |
|---|---|
| hE7.5 | 527.25 ± 71.3953 |
| hE15 | 425.64 ± 64.6798 |
| hE30 | 320.99 ± 46.2236 |
| Normal Control (NC) | 195.95 ± 19.0464 |
| Asthma-induced (OVA) | 1907.34 ± 85.3287 |
| Comparative 1 (DEXA) | 308.77 ± 49.0266 |
| Comparative 2 (Monte) | 537.98 ± 72.4581 |

PREPARATION EXAMPLE 1

Preparation of Pharmaceutical Formulations

<1-1> Powder Preparation 2 mg of styraxlignolide A compound of the present invention 1 g of lactose The above ingredients are mixed, and filled into an airtight bag to prepare a powder.

<1-2> Tablet Preparation 100 mg of styraxlignolide A compound of the present invention 100 mg of corn starch 100 mg of lactose 2 mg of magnesium stearate The above ingredients are mixed, and tableted according to a conventional tablet preparation method to prepare a tablet.

<1-3> Capsule Preparation 100 mg of homoegonol compound of the present invention 100 mg of corn starch 100 mg of lactose 2 mg of magnesium stearate The above ingredients are mixed, and filled in a gelatin capsule according to a conventional capsule preparation method to prepare a capsule.

<1-4> Pill Preparation 1 mg of homoegonol compound of the present invention 1.5 g of lactose 1 g of glycerin 0.5 g of xylitol The above ingredients are mixed to prepare a pill (4 g per pill) according to a conventional pill preparation method.

<1-5> Granule Preparation 150 mg of homoegonol compound of the present invention 50 mg of soybean extracts 200 mg of glucose 600 mg of starch The above ingredients are mixed, 100 mg of 30% ethanol is added thereto, and the mixture is dried at 60° C. to form granules, and then filled into a bag.

PREPARATION EXAMPLE 2

Preparation of Foods

Foods containing styraxlignolide A compound of the present invention are prepared as follows.

<2-1> Preparation of Wheat Flour Foods 0.5-5.0 parts by weight of styraxlignolide A compound of the present invention were added to wheat flour, and bread, cakes, cookies, crackers, and noodles were prepared using the mixture.

<2-2> Preparation of Soups and Gravies 0.1-5.0 parts by weight of styraxlignolide A compound of the present invention were added to soups and gravies to prepare processed meat products for health promotion, soups and gravies for noodles <2-3> Preparation of Ground Beef 10 parts by weight of styraxlignolide A compound of the present invention were added to ground beef to prepare ground beef for health promotion.

<2-4> Preparation of Dairy Products

Various dairy products such as butter and ice cream were prepared by adding 5-10 parts by weight of styraxlignolide A compound of the present invention to milk and using the mixture.

<2-5> Preparation of Sunsik (Grain Powder)

Brown rice, barley, glutinous rice and coix (job's tear) were gelatinized by a conventional method, followed by drying. The dried mixture was distributed and pulverized, resulting in 60-mesh size grain powders.

Black bean, black sesame and perilla were steamed and dried by a conventional method. The dried mixture was distributed and pulverized, resulting in 60-mesh size grain powders.

Styraxlignolide A compound of the present invention was vacuum-concentrated under reduced pressure using a vacuum concentrator, which was then spray-dried with a hot-air drier. The dried material was pulverized by a grinder, resulting in 60-mesh size grain powders.

The prepared grain, seeds, and styraxlignolide A compound were mixed at the following ratio.

Grain (brown rice 30 parts by weight, coix 15 parts by weight, barley 20 parts by weight), Seeds (perilla 7 parts by weight, black bean 8 parts by weight, black sesame 7 parts by weight), Styraxlignolide A compound (3 parts by weight),

*Ganoderma lucidum* (0.5 parts by weight),

*Rehmannia glutinosa* (0.5 parts by weight).

PREPARATION EXAMPLE 3

Preparation of Beverages

<3-1> Preparation of Health Beverages

Minor ingredients such as high fructose corn syrup (0.5%), oligosaccharide (2%), sugar (2%), salt (0.5%) and water (75%) were mixed homogeneously with 5 mg of homoegonol of the present invention, followed by flash pasteurization. The mixture was put in a small container such as a glass bottle or PET bottle, resulting in health beverages.

<3-2> Preparation of Vegetable Juice 5 mg of homoegonol compound of the present invention was added to 1,000 mL of tomato or carrot juice to prepare vegetable juice.

<3-3> Preparation of Fruit Juice 1 mg of homoegonol compound of the present invention was added to 1,000 mL of apple or grape juice to prepare fruit juice.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for treating asthma, the method comprising administering a pharmaceutical composition containing a pharmaceutically effective amount of styraxlignolide A compound, which is represented by the following Chemical Formula 1, an aglycone thereof, which is homoegonol represented by the following Chemical Formula 2, or a pharmaceutically acceptable salt thereof as an active ingredient to an individual having athsma:

[Chemical Formula 1]

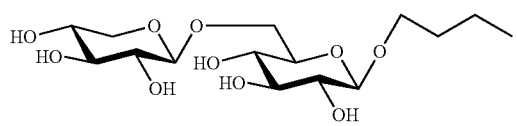

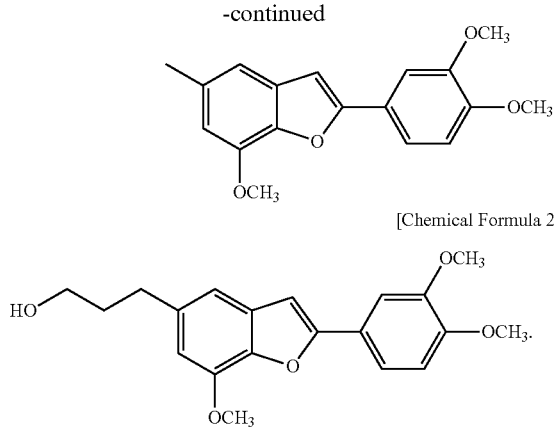

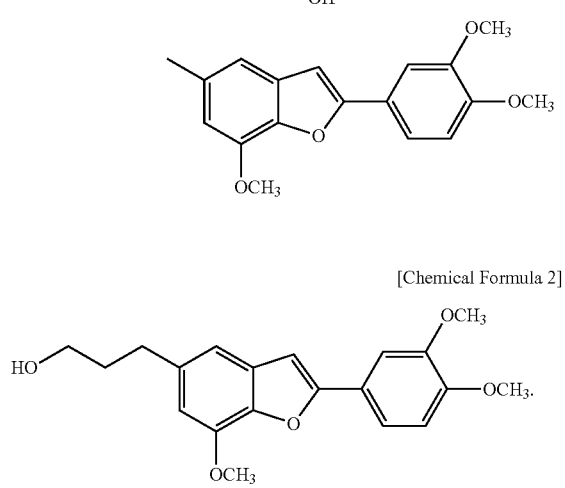

2. The method as set forth in claim 1, wherein the styraxlignolide A compound is separated from *Styrax japonica*.

3. The method as set forth in claim 1, wherein asthma is one in which airway remodeling has progressed.

4. A method for treating inflammation, related to asthma, the method comprising administering a pharmaceutical composition containing a pharmaceutically effective amount of styraxlignolide A compound, which is represented by the following Chemical formula 1, an aglycone thereof, which is homoegonol represented by the following Chemical formula 2, or a pharmaceutically acceptable salt thereof as an active ingredient to an individual having inflammation related to asthma:

5. The method as set forth in claim 4, wherein the styraxlignolide A compound is separated from *Styrax japonica*.

\* \* \* \* \*